(12) United States Patent
Ulrich

(10) Patent No.: US 7,138,399 B2
(45) Date of Patent: Nov. 21, 2006

(54) ALKOXYPYRIDINE-DERIVATIVES

(75) Inventor: Wolf-Rüdiger Ulrich, Constance (DE)

(73) Assignee: Altana Pharma AG, Constance (DE)

( * ) Notice: Subject to any disclaimer, the term of this patent is extended or adjusted under 35 U.S.C. 154(b) by 82 days.

(21) Appl. No.: 10/509,396

(22) PCT Filed: Mar. 25, 2003

(86) PCT No.: PCT/EP03/03076

§ 371 (c)(1),
(2), (4) Date: Sep. 24, 2004

(87) PCT Pub. No.: WO03/080607

PCT Pub. Date: Oct. 2, 2003

(65) Prior Publication Data

US 2005/0171125 A1    Aug. 4, 2005

(30) Foreign Application Priority Data

Mar. 27, 2002    (EP) .................. 02007049

(51) Int. Cl.
*C07D 471/04* (2006.01)
*A61K 31/4427* (2006.01)

(52) U.S. Cl. ............... 514/261; 514/303; 544/264; 546/118

(58) Field of Classification Search .......... 546/118; 544/264; 514/261, 303
See application file for complete search history.

(56) References Cited

FOREIGN PATENT DOCUMENTS

| | | |
|---|---|---|
| DE | 25 04 252 | 8/1975 |
| EP | 0 125 756 | 11/1984 |
| EP | 0 206 415 | 12/1986 |
| WO | WO 9725030 A * | 7/1987 |
| WO | WO 97/25030 | 7/1997 |

OTHER PUBLICATIONS

Deng et al, Chemical Abstracts 123: 340706, Abstract of Yaoxue Xuebao, vol. 30, No. 5, 347-356, 1995.*

* cited by examiner

*Primary Examiner*—Zinna N. Davis
(74) *Attorney, Agent, or Firm*—Nath & Associates PLLC; Joshua B. Goldberg; Sheldon M. McGee

(57) ABSTRACT

The compounds of formula I

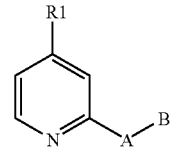

(I)

in which R1 is 1–4C-alkoxy, A is 1–4C-alkylene, B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, are effective iNOS inhibitors.

10 Claims, No Drawings

ALKOXYPYRIDINE-DERIVATIVES

This application was filed under 35 U.S.C. 371 as a national stage of PCT/EP03/03076, filed Mar. 25, 2003.

FIELD OF APPLICATION OF THE INVENTION

The invention relates to novel alkoxy-pyridine derivatives, which are used in the pharmaceutical industry for the production of pharmaceutical compositions.

KNOWN TECHNICAL BACKGROUND

In the German Patent Application DE 2504252 and in the European Patent Application EP 0125756 3H-imidazo[4,5-b]pyridine derivatives with anti-ulcer activity are described.

DESCRIPTION OF THE INVENTION

It has now been found that the alkoxy-pyridine derivatives, which are described in greater details below, have surprising and particularly advantageous properties.

The invention thus relates to compounds of formula I

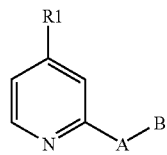

(I)

in which
R1 is 1–4C-alkoxy,
A is 1–4C-alkylene,
B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where
R2 is halogen, hydroxyl, nitro, amino, 1–7C-alkyl, trifluoromethyl, 3–7C-cycloalkyl, 3–7C-cycloalkyl-1–4C-alkyl, 1–4C-alkoxy, 1–4C-alkoxy which is completely or predominantly substituted by fluorine, 1–4C-alkoxy-1–4C-alkyl, 1–4C-alkoxy-1–4C-alkoxy, 1–4C-alkoxycarbonyl, mono- or di-1–4C-alkylaminocarbonyl, mono- or di-1–4C-alkylaminosulfonyl, 1–4C-alkylcarbonylamino, 1–4C-alkylsulfonylamino, phenyl, phenyl substituted by R21 and/or R211, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where
R21 is cyano, halogen, carboxyl, 1–4C-alkyl, 1–4C-alkoxy, aminocarbonyl, mono- or di-1–4C-alkylaminocarbonyl, 1–4C-alkylcarbonylamino, 1–4C-alkoxycarbonyl, aminosulfonyl, mono- or di-1–4C-alkylaminosulfonyl, amino, mono- or di-1–4C-alkylamino, trifluoromethyl, hydroxyl, phenylsulfonylamino or phenyl-1–4C-alkoxy,
R211 is halogen or 1–4C-alkoxy,
R22 is halogen, 1–4C-alkyl or 1–4C-alkoxy,
R23 is halogen, 1–4C-alkyl or 1–4C-alkoxy,
R24 is halogen, 1–4C-alkyl or 1–4C-alkoxy,
R3 is halogen, 1–4C-alkyl or 1–4C-alkoxy,
R4 is halogen, amino, 1–4C-alkyl, 1–4C-alkoxy or phenyl,
R5 is halogen, 1–4C-alkyl or 1–4C-alkoxy, the salts, N-oxides and the salts of the N-oxides of these compounds.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–7C-Alkyl is a straight-chain or branched alkyl radical having 1 to 7 carbon atoms. Examples are the heptyl, isoheptyl(5-methylhexyl), hexyl, isohexyl(4-methylpentyl), neohexyl(3,3-dimethylbutyl), pentyl, isopentyl(3-methylbutyl), neopentyl(2,2-dimethylpropyl), butyl, isobutyl, sec-butyl, tert-butyl, propyl, isopropyl, ethyl and methyl radicals.

1–4C-Alkylene is a straight chain alkylene radical having 1 to 4 carbon atoms. Examples which may be mentioned in this context are the methylene (—CH$_2$—), ethylene (—CH$_2$—CH$_2$—), trimethylene (—CH$_2$—CH$_2$—CH$_2$—) and the tetramethylene (—CH$_2$—CH$_2$—CH$_2$—CH$_2$—) radical.

1–4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, iso-propoxy, ethoxy and methoxy radicals.

3–7C-Cycloalkyl stands for cyclopropyl, cyclobutyl, cyclopentyl, cyclohexyl and cycloheptyl, of which cyclopropyl, cyclobutyl and cyclopentyl are preferred.

3–7C-Cycloalkyl-1–4C-alkyl stands for one of the abovementioned 1–4C-alkyl radicals, which is substituted by one of the abovementioned 3–7C-cycloalkyl radicals. 3–7C-Cycloalkyl-1–2C-alkyl, particularly 3–7C-cycloalkylmethyl, radicals are to be emphasized in this connection. Examples which may be mentioned are the cyclopropylmethyl, the cyclohexylmethyl and the cyclohexylethyl radicals.

Halogen within the meaning of the present invention is iodine, bromine, chlorine or fluorine.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy groups are replaced by fluorine atoms.

1–4C-Alkoxy-1–4C-alkoxy stands for one of the abovementioned 1–4C-alkoxy radicals which is substituted by the same or another of the abovementioned 1–4C-alkoxy radicals. Examples which may be mentioned are the 2-(methoxy)ethoxy (—O—CH$_2$—CH$_2$—O—CH$_3$) and the 2-(ethoxy)ethoxy radical (—O—CH$_2$—CH$_2$—O—CH$_2$—CH$_3$).

1–4C-Alkoxy-1–4C-alkyl stands for one of the abovementioned 1–4C-alkyl radicals which is substituted by one of the abovementioned 1–4C-alkoxy radicals. Examples which may be mentioned are the 2-ethoxyethyl and the 3-methoxypropyl radical.

Mono- or Di-1–4C-alkylamino radicals contain in addition to the nitrogen atom, one or two of the abovementioned 1–4C-alkyl radicals. Preferred are the di-1–4C-alkylamino radicals, especially the dimethylamino, the diethylamino and the diisopropylamino radical.

Mono- or Di-1–4C-alkylaminocarbonyl radicals contain in addition to the carbonyl group one of the abovementioned mono- or di-1–4C-alkylamino radicals. Examples which may be mentioned are the N-methyl- the N,N-dimethyl-, the N-ethyl-, the N-propyl-, the N,N-diethyl- and the N-isopropylaminocarbonyl radical.

Mono- or Di-1–4C-alkylaminosulfonyl stands for a sulfonyl group to which one of the above-mentioned mono- or di-1–4C-alkylamino radicals is bonded. Examples which may be mentioned are the methylaminosulfonyl, the dimethylaminosulfonyl and the ethylaminosulfonyl radical.

An 1–4C-Alkylcarbonylamino radical is, for example, the propionylamino [$C_3H_7C(O)NH$—] and the acetylamino radical [$CH_3C(O)_2NH$—].

An 1–4C-Alkylsulfonylamino radical is, for example, the propylsulfonylamino [$C_3H_7S(O)_2NH$—] and the methylsulfonylamino radical [$CH_3S(O)_2NH$—].

1–4C-Alkoxycarbonyl is a carbonyl group to which one of the abovementioned 1–4C-alkoxy radicals is bonded. Examples are the methoxycarbonyl [$CH_3O$—$C(O)$—] and the ethoxycarbonyl [$CH_3CH_2O$—$C(O)$—] radical.

Phenyl-1–4C-alkoxy stands for one of the abovementioned 1–4C-alkoxy radicals, which is substituted by the phenyl radical. Examples which may be mentioned are the benzyloxy and the phenethoxy radical.

Phenyl-1–4C-alkyl stands for one of the abovementioned 1–4C-alkyl radicals, which is substituted by a phenyl radical. Examples which may be mentioned are the phenylethyl and the benzyl radical.

Pyridyl-1–4C-alkyl stands for one of the abovementioned 1–4C-alkyl radicals, which is substituted by a pyridyl radical. Examples which may be mentioned are the pyridylethyl and the pyridylmethyl radical.

N-oxide denotes the N-oxide on the pyridine which is substituted by R1.

3H-imidazo[4,5-b]pyridin-2-yl radicals substituted by R2 and/or R3 which may be mentioned are 7-methyl-3H-imidazo[4,5-b]pyridin-2-yl, 5,7-dimethyl-3H-imidazo[4,5-b]pyridin-2-yl, 5-methoxy-3H-imidazo[4,5-b]pyridin-2-yl, 6-brom-3H-imidazo[4,5-b]pyridin-2-yl, 7-methoxy-3H-imidazo[4,5-b]pyridin-2-yl, 7-hydroxy-3H-imidazo[4,5-b]pyridin-2-yl, 7-ethoxy-3H-imidazo[4,5-b]pyridin-2-yl, 7-methoxy-ethoxy-imidazo[4,5-b]pyridin-2-yl, 7-(1,1,1-trifluoroethoxy)-3H-imidazo[4,5-b]pyridin-2-yl, 7-(phenylethoxy)-3H-imidazo[4,5-b]pyridin-2-yl, 7-(phenylethyl)-3H-imidazo[4,5-b]pyridin-2-yl, 7-(tolylethyl)-3H-imidazo[4,5-b]pyridin-2-yl, 7-(pyrid-4-ylethyl)-3H-imidazo[4,5-b]pyridin-2-yl, 7-(pyrid-2-ylethyl)-3H-imidazo[4,5-b]pyridin-2-yl, 7-(pyrid-3-ylethyl)-3H-imidazo[4,5-b]pyridin-2-yl, 7-(4-methoxypyrid-2-ylethyl)-3H-imidazo[4,5-b]pyridin-2-yl, 6-phenyl-3H-imidazo[4,5-b]pyridin-2-yl, 6-n-butyl-3H-imidazo[4,5-b]pyridin-2-yl, 6-(4-methoxyphenyl)-3H-imidazo[4,5-b]pyridin-2-yl, 6-(4-methylphenyl)-3H-imidazo[4,5-b]pyridin-2-yl, 6-nitro-3H-imidazo[4,5-b]pyridin-2-yl, 6-(pyrid-3-yl)-3H-imidazo[4,5-b]pyridin-2-yl, 6-(4-cyanophenyl)-3H-imidazo[4,5-b]pyridin-2-yl, 6-methyl-3H-imidazo[4,5-b]pyridin-2-yl, 6-trifluoromethyl-3H-imidazo[4,5-b]pyridin-2-yl, 6-iodo-3H-imidazo[4,5-b]pyridin-2-yl, 6-(4-aminophenyl)-3H-imidazo[4,5-b]pyridin-2-yl, 6-(4-dimethylaminophenyl)-3H-imidazo[4,5-b]pyridin-2-yl, 6-(4-hydroxyphenyl)-3H-imidazo[4,5-b]pyridin-2-yl, 6-(4-trifluorophenyl)-3H-imidazo[4,5-b]pyridin-2-yl, 6-(4-phenylsulfonylaminophenyl)-3H-imidazo[4,5-b]pyridin-2-yl, 6-(3,4-dimethoxyphenyl)-3H-imidazo[4,5-b]pyridin-2-yl, 6-(3,4-dichlorophenyl)-3H-imidazo[4,5-b]pyridin-2-yl, 6-(3,5-dichlorophenyl)-3H-imidazo[4,5-b]pyridin-2-yl, 6-(4-benzyloxyphenyl)-3H-imidazo[4,5-b]pyridin-2-yl or 6-(4-benzyloxy-3-fluoro-phenyl)-3H-imidazo[4,5-b]pyridin-2-yl.

9H-purin-8-yl radicals substituted by R4 and/or R5 which may be mentioned are 6-methoxy-9H-purin-8-yl, 6-ethoxy-9H-purin-8-yl, 2-methyl-9H-purin-8-yl, 2-ethyl-9H-purin-8-yl, 2-amino-9H-purin-8-yl, 2-chloro-9H-purin-8-yl and 2-phenyl-9H-purin-8-yl.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

A person skilled in the art knows on the base of his/her expert knowledge that the compounds according to this invention can exist, with regard to the fused imidazo ring, in different tautomeric forms such as e.g. in the 1-H form or, preferably, in the 3-H form. The invention includes all conceivable tautomers in pure form as well as in any mixing ratio. Particularly the present invention includes the pure 1-H and, preferably, 3-H-tautomers as well as any mixtures thereof.

An embodiment (embodiment a) of the invention are compounds of the formula I in which R1 is methoxy, A is ethylene, B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where R2 is halogen, hydroxyl, nitro, 1–7C-alkyl, trifluoromethyl, 3–7C-cycloalkyl, 3–7C-cycloalkyl-1–4C-alkyl, 1–4C-alkoxy, 1–4C-alkoxy which is completely or predominantly substituted by fluorine, 1–4C-alkoxy-1–4C-alkyl, 1–4C-alkoxy-1–4C-alkoxy, 1–4C-alkoxycarbonyl, phenyl, phenyl substituted by R21 and/or R211, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where
R21 is cyano, halogen, carboxyl, 1–4C-alkyl, 1–4C-alkoxy, aminocarbonyl, mono- or di-1–4C-alkylaminocarbonyl, 1–4C-alkylcarbonylamino, 1–4C-alkoxycarbonyl, amino, mono- or di-1–4C-alkylamino, trifluoromethyl, hydroxyl, phenylsulfonylamino or phenyl-1–4C-alkoxy,
R211 is halogen or 1–4C-alkoxy,
R22 is halogen, 1–4C-alkyl or 1–4C-alkoxy,
R23 is 1–4C-alkyl,
R24 is halogen, 1–4C-alkyl or 1–4C-alkoxy,
R3 is halogen, 1–4C-alkyl or 1–4C-alkoxy,
R4 is halogen, 1–4C-alkyl or 1–4C-alkoxy,
R5 is halogen or 1–4C-alkyl, the salts, the N-oxides and the salts of the N-oxides of these compounds.

Compounds of embodiment a to be emphasized are those compounds of formula I in which
R1 is methoxy,
A is ethylene,
B represents 3H-imidazo[4,5-b]pyridin-2-yl, 3H-imidazo[4,5-b]pyridin-2-yl substituted by R2 and/or R3 or 9H-purin-8-yl, where
R2 is halogen, hydroxyl, nitro, 1–7C-alkyl, trifluoromethyl, 3–7C-cycloalkyl-1–4C-alkyl, 1–4C-alkoxy, 1–4C-alkoxy which is completely or predominantly substituted by fluorine, 1–4C-alkoxy-1–4C-alkoxy, 1–4C-alkoxycarbonyl, phenyl, phenyl substituted by R21 and/or R211, phenyl-1–4C-alkyl, phenyl-1–4C-alkyl wherein the phenyl moiety is substituted by R22, phenyl-1–4C-alkoxy, pyridyl, pyridyl-1–4C-alkyl, pyridyl-1–4C-alkyl wherein the pyridyl moiety is substituted by R24, where
R21 is cyano, halogen, carboxyl, 1–4C-alkyl, 1–4C-alkoxy, 1–4C-alkylcarbonylamino, 1–4C-alkoxycarbonyl, amino, mono- or di-1–4C-alkylamino, trifluoromethyl, hydroxyl, phenylsulfonylamino or phenyl-1–4C-alkoxy,
R211 is halogen or 1–4C-alkoxy,
R22 is halogen or 1–4C-alkyl,
R24 is 1–4C-alkoxy,
R3 is 1–4C-alkyl, the salts, the N-oxides and the salts of the N-oxides of these compounds.

Compounds of embodiment a to be particularly emphasized are those compounds of formula I in which
R1 is methoxy,
A is ethylene,
B represents 3H-imidazo[4,5-b]pyridin-2-yl, 3H-imidazo[4,5-b]pyridin-2-yl substituted by R2 and/or R3 or 9H-purin-8-yl, where
R2 is iodine, bromine, hydroxyl, nitro, methyl, ethyl, butyl, isobutyl, pentyl, isopentyl, trifluoromethyl, cyclohexylmethyl, methoxy, ethoxy, 2,2,2-trifluoroethoxy, methoxyethoxy, methoxycarbonyl, phenyl, phenyl substituted by R21 and/or R211, phenylethyl, benzyl, phenylpropyl, phenylethyl wherein the phenyl moiety is substituted by R22, benzyl wherein the phenyl moiety is substituted by R22, phenylethoxy, pyridyl, pyridylethyl, pyridylethyl wherein the pyridyl moiety is substituted by R24, where
R21 is cyano, fluorine, chlorine, bromine, carboxyl, methyl, methoxy, acetylamino, methoxycarbonyl, amino, dimethylamino, trifluoromethyl, hydroxyl, phenylsulfonylamino or benzyloxy,
R211 is chlorine, fluorine or methoxy,
R22 is bromine or methyl,
R24 is methoxy,
R3 is methyl, the salts, the N-oxides and the salts of the N-oxides of these compounds.

A further embodiment (embodiment b) of the invention are compounds of the formula I in which
R1 is 1–4C-alkoxy,
A is 1–4C-alkylene,
B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where
R2 is chlorine, bromine, fluorine, hydroxyl, nitro, amino, 1–7C-alkyl, trifluoromethyl, 3–7C-cycloalkyl, 3–7C-cycloalkyl-1–4C-alkyl, 1–4C-alkoxy, 1–4C-alkoxy which is completely or predominantly substituted by fluorine, 1–4C-alkoxy-1–4C-alkyl, 1–4C-alkoxy-1–4C-alkoxy, mono- or di-1–4C-alkylaminocarbonyl, mono- or di-1–4C-alkylaminosulfonyl, 1–4C-alkylcarbonylamino, 1–4C-alkylsulfonylamino, phenyl, phenyl substituted by R21, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where
R21 is cyano, chlorine, bromine, fluorine, carboxyl, 1–4C-alkyl, 1–4C-alkoxy, aminocarbonyl, mono- or di-1–4C-alkylaminocarbonyl, 1–4C-alkylcarbonylamino, 1–4C-alkoxycarbonyl, aminosulfonyl or mono- or di-1–4C-alkylaminosulfonyl,
R22 is chlorine, bromine, fluorine, 1–4C-alkyl or 1–4C-alkoxy,
R23 is chlorine, bromine, fluorine, 1–4C-alkyl or 1–4C-alkoxy,
R24 is chlorine, bromine, fluorine, 1–4C-alkyl or 1–4C-alkoxy,
R3 is chlorine, bromine, fluorine, 1–4C-alkyl or 1–4C-alkoxy,
R4 is chlorine, bromine, fluorine, 1–4C-alkyl, 1–4C-alkoxy or phenyl,
R5 is chlorine, bromine, fluorine, 1–4C-alkyl or 1–4C-alkoxy, the salts, the N-oxides and the salts of the N-oxides of these compounds.

Compounds of embodiment b, which are to be emphasized, are those compounds of formula I in which
R1 is methoxy,
A is ethylene,
B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where
R2 is chlorine, bromine, fluorine, nitro, 1–7C-alkyl, trifluoromethyl, 1–4C-alkoxy, 1–4C-alkoxy which is completely or predominantly substituted by fluorine, 1–4C-alkoxy-1–4C-alkyl, 1–4C-alkoxy-1–4C-alkoxy, phenyl, phenyl substituted by R21, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where
R21 is cyano, chlorine, bromine, fluorine, carboxyl, 1–4C-alkyl, 1–4C-alkoxy, aminocarbonyl, mono- or di-1–4C-alkylaminocarbonyl, 1–4C-alkylcarbonylamino or 1–4C-alkoxycarbonyl,
R22 is chlorine, bromine, fluorine, 1–4C-alkyl or 1–4C-alkoxy, R23 is 1–4C-alkyl,
R24 is chlorine, bromine, fluorine, 1–4C-alkyl or 1–4C-alkoxy,
R3 is 1–4C-alkyl,
R4 is chlorine, bromine, fluorine, 1–4C-alkyl or 1–4C-alkoxy,
R5 is chlorine, bromine, fluorine or 1–4C-alkyl, the salts, the N-oxides and the salts of the N-oxides of these compounds.

Compounds of embodiment b, which are particularly to be emphasized, are those compounds of formula I in which
R1 is methoxy,
A is ethylene,
B is 3H-imidazo[4,5-b]pyridin-2-yl, 7-methyl-3H-imidazo[4,5-b]pyridin-2-yl, 5,7-dimethyl-3H-imidazo[4,5-b]pyridin-2-yl, 5-methoxy-3H-imidazo[4,5-b]pyridin-2-yl, 6-bromo-3H-imidazo[4,5-b]pyridin-2-yl or 9H-purin-8-yl, the salts, the N-oxides and the salts of the N-oxides of these compounds.

Preferred compounds of formula I are
2-[2-(4-methoxypyridin-2-yl)ethyl]-3H-imidazo[4,5-b]pyridine,
8-[2-(4-methoxypyridin-2-yl)ethyl]-9H-purine,
2-[2-(4-methoxypyridin-2-yl)ethyl]-7-methyl-3H-imidazo[4,5-b]pyridine,
2-[2-(4-methoxypyridin-2-yl)ethyl]-5,7-dimethyl-3H-imidazo[4,5-b]pyridine,
2-[2-(4-methoxypyridin-2-yl)ethyl]-5-methoxy-3H-imidazo[4,5-b]pyridine,
2-[2-(4-methoxypyridin-2-yl)ethyl]-6-bromo-3H-imidazo[4,5-b]pyridine,
2-[2-(4-methoxypyridin-2-yl)ethyl]-6-iodo-3H-imidazo[4,5-b]pyridine,
2-[2-(4-methoxypyridin-2-yl)ethyl]-6-nitro-3H-imidazo[4,5-b]pyridine,
2-[2-(4-methoxypyridin-2-yl)ethyl]-6-trifluoromethyl-3H-imidazo[4,5-b]pyridine,
2-[2-(4-methoxypyridin-2-yl)ethyl]-6-phenyl-3H-imidazo[4,5-b]pyridine,
2-[2-(4-methoxypyridin-2-yl)ethyl]-6-methyl-3H-imidazo[4,5-b]pyridine,
2-[2-(4-methoxypyridin-2-yl)ethyl]-6-(2-methylpropyl)-3H-imidazo[4,5-b]pyridine,
2-[2-(4-methoxypyridin-2-yl)ethyl]-6-cyclohexylmethyl-3H-imidazo[4,5-b]pyridine,
2-[2-(4-methoxypyridin-2-yl)ethyl]-6-(2-phenylethyl)-3H-imidazo[4,5-b]pyridine,
2-[2-(4-methoxypyridin-2-yl)ethyl]-6-(3,4-dichlorphenyl)-3H-imidazo[4,5-b]pyridine,
2-[2-(4-methoxypyridin-2-yl)ethyl]-6-(4-bromphenyl)-3H-imidazo[4,5-b]pyridine,
2-[2-(4-methoxypyridin-2-yl)ethyl]-6-(4-brombenyl)-3H-imidazo[4,5-b]pyridine,
7-(2-methoxyethoxy)-2-[2-(4-methoxypyridin-2-yl)ethyl]-3H-imidazo[4,5-b]pyridine,
2-[2-(4-methoxypyridin-2-yl)ethyl]-7-(2-phenylethoxy)-3H-imidazo[4,5-b]pyridine,
2-[2-(4-methoxypyridin-2-yl)ethyl]-7-(2,2,2-trifluoroethoxy)-3H-imidazo[4,5-b]pyridine,
7-hydroxy-2-[2-(4-methoxypyridin-2-yl)ethyl]-3H-imidazo[4,5-b]pyridine,
2-[2-(4-methoxypyridin-2-yl)ethyl]-7-(2-p-tolylethyl)-3H-imidazo[4,5-b]pyridine,
2,7-bis-[2-(4-methoxypyridin-2-yl)ethyl]-3H-imidazo[4,5-b]pyridine,
2-[2-(4-methoxypyridin-2-yl)ethyl]-7-(2-pyridin-2-yl-ethyl)-3H-imidazo[4,5-b]pyridine,
2-[2-(4-methoxypyridin-2-yl)ethyl]-6-p-tolyl-3H-imidazo[4,5-b]pyridine,
2-[2-(4-methoxypyridin-2-yl)ethyl]-6-(pyridin-3-yl)-3H-imidazo-[4,5-b]pyridine,
2-[2-(4-methoxypyridin-2-yl)ethyl]-6-(4-aminophenyl)-3H-imidazo-[4,5-b]pyridine,
2-[2-(4-methoxypyridin-2-yl)ethyl]-6-(4-hydroxyphenyl)-3H-imidazo-[4,5-b]pyridine,
2-[2-(4-methoxypyridin-2-yl)ethyl]-6-(4-N,N-dimethylaminophenyl)-3H-imidazo[4,5-b]pyridine,
2-[2-(4-methoxypyridin-2-yl)ethyl]-6-(4-trifluormethylphenyl)-3H-imidazo[4,5-b]pyridine,
2-[2-(4-methoxypyridin-2-yl)ethyl]-6-(3,4-dimethoxyphenyl)-3H-imidazo[4,5-b]pyridine,
2-[2-(4-methoxypyridin-2-yl)ethyl]-6-(4-benzyloxyphenyl)-3H-imidazo[4,5-b]pyridine,
2-[2-(4-methoxypyridin-2-yl)ethyl]-6-(4-benzyloxy-3-fluorophenyl)-3H-imidazo[4,5-b]pyridine,
2-[2-(4-methoxypyridin-2-yl)ethyl]-6-(4-cyanophenyl)-3H-imidazo[4,5-b]pyridine,
2-[2-(4-methoxypyridin-2-yl)ethyl])-3H-imidazo[4,5-b]pyridine-6-carboxylic acid methyl ester,
N-(4-{2-[2-(4-methoxypyridin-2-yl)ethyl]-3H-imidazo[4,5-b]pyridin-6-yl}phenyl)-acetamide,
N-(4-{2-[2-(4-methoxypyridin-2-yl)ethyl]-3H-imidazo[4,5-b]pyridin-6-yl}phenyl)-benzenesulfonamide,
2-[2-(4-methoxy-1-oxy-pyridin-2-yl)ethyl])-3H-imidazo[4,5-b]pyridine, the salts, the N-oxides and the salts of the N-oxides of these compounds.

A special embodiment of the compounds of the present invention include those compounds of formula I in which R1 is methoxy.

Another special embodiment of the compounds of the present invention include those compounds of formula I in which A is ethylene.

A further special embodiment of the compounds of the present invention include those compounds of formula I in which R1 is methoxy and A is ethylene.

Another further special embodiment of the compounds of the present invention include those compounds of formula I in which R1 is methoxy, A is ethylene and B represents 3H-imidazo[4,5-b]pyridin-2-yl or 3H-imidazo[4,5-b]pyridin-2-yl substituted by R2 and/or R3.

Still a further special embodiment of the compounds of the present invention include those compounds of formula I in which R1 is methoxy, A is ethylene and B represents 9H-purin-8-yl or 9H-purin-8-yl substituted by R4 and/or R5.

The compounds of formula I according to the invention can, for example, be prepared as described below in this specification (e.g. as described in detail by way of example in the following examples) and/or shown in the following reaction scheme or similarly or analogously thereto.

In the following reaction scheme the synthesis of compounds of formula I in which R1 is 1–4C-alkoxy, A is ethylene and B is an unsubstituted or by R2 and/or R3 substituted 3H-imidazo[4,5-b]pyridin-2-yl radical is described.

In a first reaction step the nitro group of the commercially available 4-nitro-2-picoline-N-oxide is exchanged by an 1–4C-alkoxy group. The resulting 4-(1–4C)-alkoxy-2-picoline-N-oxide (compound of formula VIII) is then via a rearrangement and an oxidation step converted to 4-(1–4C)-alkoxy-pyridin-2-carbaldehyde (compound of formula VI).

The carbon chain in 2-position of the compounds of formula VI is lengthened, for example, by a condensation (with a malonic acid derivative) and a subsequent hydrogenation reaction. Alternatively, the carbon chain can be lengthened using a Wittig reaction followed by a hydrogenation reaction.

In the last step the methyl 3-(4-(1–4C)-alkoxypyridin-2-yl)propionate (compound of formula IV) or the corresponding acid (compound of formula II) are converted with a 2,3-diaminopyridine derivative (compounds of formula II) to give compounds of formula I.

Compounds of formula II, in which R2 and R3 have the meanings indicated above are known or can be prepared in a known manner or analogously or similarly to art-known processes or as described in the following examples.

Compounds of formula I, in which B represents an unsubstituted or by R4 and/or R5 substituted 9H-purin-8-yl radical instead of an unsubstituted or by R2 and/or R3 substituted 3H-imidazo[4,5-b]pyridin-2-yl radical can be prepared analogously to the synthesis routes shown and/or specified in this specification using an 5,6-diaminopyrimidine derivative instead of the 2,3-diaminopyridine derivative.

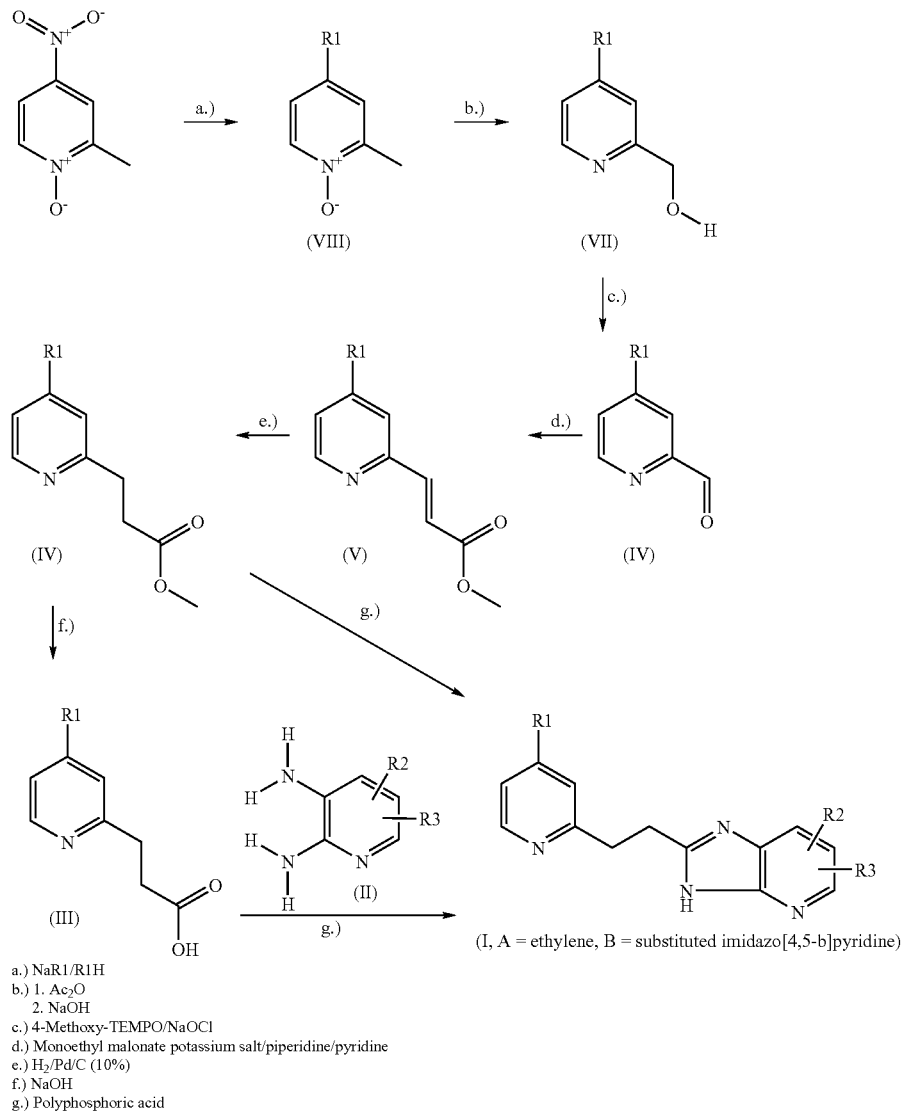

The synthesis of 4-methoxy-pyridin-2-carbaldehyde (compound of formula VI) is described for example in Ashimori et al, Chem Pharm Bull 38, 2446–2458 (1990).

The synthesis of 3-(4-methoxypyridin-2-yl)propionic acid (compound of formula II) is described in the paragraph Starting Compounds.

a.) NaR1/R1H  b.) 1. Ac$_2$O  2. NaOH  c.) 4-Methoxy-TEMPO/NaOCl d.) Monoethyl malonate potassium salt/piperidine/pyridine e.) H$_2$/Pd/C (10%)  f.) NaOH  g.) Polyphosphoric acid Compounds of formula I, in which R2 is phenyl substituted by R21, can be prepared, for example, as described by way of example in the following examples or according to processes known from literature or analogously or similarly thereto, for example starting from the corresponding compounds of formula I, in which R2 or R3 is halogen, preferably iodine or bromine, e.g. according to known metal catalyzed CC-coupling reactions, such as e.g. the Suzuki reaction is. This Suzuki reaction can be carried out as known to the person skilled in the art or as described in the following examples using, for example, appropriate boronic acids or boronic acid derivatives and suitable metal catalysts, preferably transition metal catalysts (such as, for example, palladium catalysts), optionally, in the presence of an inorganic lithium salt, preferably lithium chloride. Said boronic acids or boronic acid derivatives can be prepared according to art-known manners, e.g. such as described in the following examples from R21-substituted phenyl halides or triflates using e.g. bis-(pinacolato)-diboron.

Compounds of formula I, in which R2 is 1–4C-alkoxycarbonyl, can be obtained, for example, as described in the following examples or in a manner known to the person skilled in the art according, for example, a metal catalyzed (e.g. a transition metal catalyzed, preferably palladium catalyzed) carbonylation reaction of the corresponding compounds of formula I, in which R2 or R3 is halogen, preferably iodine or bromine, in the presence of a suitable alcohol.

Compounds of formula I, in which R21 is 1–4C-alkylcarbonylamino or phenylsulfonylamino, can be prepared, for example, as described by way of example in the following examples or according to processes known from literature or analogously or similarly thereto, for example starting from the corresponding compounds of formula I, in which R21 is amino, e.g. by acylation or sulfonylation reaction habitual per se to the skilled person.

The compounds of formula I can be converted, optionally, into their N-oxides, for example with the aid of hydrogen peroxide in methanol or with the aid of m-chloroperoxybenzoic acid in dichloromethane (e.g. in an analogous or similar manner as described exemplarily in the following examples). The person skilled in the art is familiar on the basis of his/her expert knowledge with the reaction conditions which are specifically necessary for carrying out the N-oxidation.

Suitably, the conversions are carried out analogously or similarly to methods which are familiar per se to the person skilled in the art, for example, in the manner which is described by way of example in the following examples.

It is known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1991.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

Moreover, the person skilled in the art knows on the base of the disclosure (e.g. the explicite, implicite or inherent disclosure) of the present invention (for example on the base of the characteristics and/or properties of the compounds according to this invention) and on the base of his/her knowledge—for example his/her knowledge in medicinal chemistry, in medicinal pharmacology, in in vivo and/or in vitro screening or testing systems and/or in methods for identifying pharmaceutically active compounds—how to identify further pharmaceutically active and acceptable compounds such as, for example, derivatives, analogues or homologues of the compounds according to this invention. All this further pharmaceutically active and acceptable compounds, such as, for example, derivatives, analogues or homologues of the compounds according to this invention, are also part of the scope of the present invention.

The following examples illustrate the invention in greater detail, without restricting it. As well, further compounds of formula I, of which the preparation is explicitly not described, can be prepared in an analogous way or in a way which is known by a person skilled in the art using customary preparation methods.

The compounds, which are mentioned in the examples as well as their salts are preferred compounds of the invention.

EXAMPLES

Final Products 1. 2-[2-(4-Methoxypyridin-2-yl)ethyl]-3H-imidazo[4,5-b]pyridine

With stirring, a mixture of 0.643 g of methyl 3-(4-methoxypyridin-2-yl)propionate (starting material A2), 0.359 g of 2,3-diaminopyridine and 10 g of polyphosphoric acid (PPA) is heated at 160° C. for 1 h. After cooling, the mixture is poured into about 50 ml of ice-water and then neutralized (pH 7–8) using 6N aqueous sodium hydroxide solution. The mixture is extracted three times with dichloromethane/methanol 9:1, the combined organic phases are evaporated to dryness and the residue is chromatographed on a silica gel column (dichloromethane/methanol 15:1). Concentration of the chromatographically pure fractions gives 0.36 g of an oil, which crystallizes on standing. The product is recrystallized from ethyl acetate/petroleum ether, giving 0.278 g of the title compound as a light-beige powder of m.p. 116–117° C.; the mass spectrum shows the molecular peaks $MH^+$ and $2MNa^+$ at 255.3 and 530.9 Da.

2. 8-[2-(4-Methoxypyridin-2-yl)ethyl]-9H-purine

Similarly to Example 1, 0.384 g of methyl 3-(4-methoxypyridin-2-yl)propionate (starting material A2), 0.216 g of 4,5-diaminopyrimidine and 4 g of PPA give, after 2 h at 140° C., 0.175 g of the title compound of m.p. 150–152° C. (from ethyl acetate/petroleum ether). The mass spectrum shows the molecular peaks MH$^+$ and 2MNa$^+$ at 256.3 and 532.8 Da.

3. 2-[2-(4-Methoxypyridin-2-yl)ethyl]-7-methyl-3H-imidazo[4,5-b]pyridine

Similarly to Example 1, 0.766 g of methyl 3-(4-methoxypyridin-2-yl)propionate (starting material A2), 0.481 g of 2,3-diamino-4-methylpyridine and 8 g of PPA give, after dilution with ice-water and neutralization, a solid which is crystallized from ethyl acetate/petroleum ether. This gives 0.495 g of the title compound of m.p. 143–144° C. The mass spectrum shows the molecular peaks MH$^+$ and 2MNa$^+$ at 269.3 and 558.9 Da.

4. 2-[2-(4-Methoxypyridin-2-yl)ethyl]-5,7-dimethyl-3H-imidazo[4,5-b]pyridine Similarly to Example 3, 0.35 g of methyl 3-(4-methoxypyridin-2-yl)propionate (starting material A2), 0.245 g of 2,3-diamino-4,6-dimethylpyridine and 3.5 g of PPA give, after dilution with ice-water and neutralization, a solid which is crystallized from ethyl acetate/petroleum ether. This gives 0.335 g of the title compound of m.p. 176–178° C. The mass spectrum shows the molecular peaks MH$^+$ and 2MNa$^+$ at 283.3 and 587.0 Da.

5. 2-[2-(4-Methoxypyridin-2-yl)ethyl]-5-methoxy-3H-imidazo[4,5-b]pyridine

Similarly to Example 1, 0.316 g of methyl 3-(4-methoxypyridin-2-yl)propionate (starting material A2), 0.225 g of 2,3-diamino-6-methoxypyridine and 4 g of PPA give, after two hours at 140° C. and chromatography using toluene/acetone 2:1, 0.103 g of the title compound of m.p. 93–95° C. (from ethyl acetate/petroleum ether). The mass spectrum shows the molecular peaks MH$^+$, MNa$^+$ and 2MNa$^+$ at 285.3, 307.2 and 591.0 Da.

6. 2-[2-(4-Methoxypyridin-2-yl)ethyl]-6-bromo-3H-imidazo[4,5-b]pyridine

Similarly to Example 1, 3.74 g of 3-(4-methoxypyridin-2-yl)propionic acid (starting material A1), 3.00 g of 2,3-diamino-5-bromopyridine and 120 g of PPA (24 hours at 140° C.) give, after dilution with ice-water and neutralization, a solid which is crystallized from ethyl acetate/petroleum ether. This gives 3.48 g of the title compound of m.p. 207–209° C. The mass spectrum shows the molecular peak MH$^+$ at 335.1 Da.

7. 2-[2-(4-Methoxypyridin-2-yl)ethyl]-6-iodo-3H-imidazo[4,5-b]pyridine

Similarly to Example 1, 4.98 g of 3-(4-methoxypyridin-2-yl)propionic acid (starting material A1), 5.88 g of 2,3-diamino-5-iodopyridine (Cugola et al., Bioorg. Med. Chem. Lett. 22, 2749–2754 (1996)) and 90 g of PPA (24 hours at 140° C.) give 7.08 g of the title compound of m.p. 206–208° C. (crystallized from 2-propanol). The mass spectrum shows the molecular peak MH$^+$ at 381.2 Da.

8. 2-[2-(4-Methoxypyridin-2-yl)ethyl]-6-nitro-3nH-imidazo[4,5-b]pyridine

Similarly to Example 1, 0.62 g of 3-(4-methoxypyridin-2-yl)propionic acid (starting material A1), 0.48 g of 2,3-diamino-5-nitropyridine (Cai et al., J. Med. Chem. 40, 3679–3686 (1997)) and 12 g of PPA (24 hours at 140° C.) give 0.115 g of the title compound of m.p. 248–249° C. The mass spectrum shows the molecular peaks MH$^+$ and 2MNa$^+$ at 300.2 and 620.7 Da.

9. 2-[2-(4-Methoxypyridin-2-yl)ethyl]-6-trifluoromethyl-3H-imidazo[4,5-b]pyridine Similarly to Example 1, 0.392 g of 3-(4-methoxypyridin-2-yl)propionic acid (starting material A1), 0.48 g of 2,3-diamino-5-trifluoromethylpyridine (starting material B1) and 12 g of PPA (24 hours at 125° C.) give 0.10 g of the title compound of m.p. 204–206°C. (crystallized from ethyl acetate/petroleum ether). The mass spectrum shows the molecular peak MH$^+$ at 323.1 Da.

10. 2-[2-(4-Methoxypyridin-2-yl)ethyl]-6-phenyl-3H-imidazo[4,5-b]pyridine

Similarly to Example 1, 0.572 g of 3-(4-methoxypridin-2-yl)propionic acid (starting material A1), 0.49 g of 2,3-diamino-5-phenylpyridine (starting material C1) and 15 g of PPA (24 hours at 110° C. and chromatography using ethyl acetate/methanol 10:1) give 0.47 g of the title compound of m.p. 182–183° C. (crystallized from ethyl acetate). The mass spectrum shows the molecular peak MH$^+$ at 331.2 Da.

11. 2-[2-(4-Methoxypyridin-2-yl)ethyl]-6-methyl-3H-imidazo[4,5-b]pyridine

Similarly to Example 1, 0.428 g of 3-(4methoxypyridin-2-yl)propionic acid (starting material A1), 0.26 g of 2,3-diamino-5-methylpyridine (Lappin et al., J. Amer. Chem Soc. 72, 2806 (1950) and 8 g of PPA (4 hours at 140° C.) give 0.25 g of the title compound of m.p. 150–152° C. (crystallized from ethyl acetate). The mass spectrum shows the molecular peaks MH$^+$ and 2MNa$^+$ at 269.3 and 559.1 Da.

12. 2-[2-(4-Methoxypyridin-2-yl)ethyl]-6-(2-methylpropyl)-3H-imidazo[4,5-b]pyridine Similarly to Example 1, 0.37 g of 3-(4-methoxypyridin-2-yl)propionic acid (starting material A1), 0.49 g of 2,3-diamino-5-(2-methylpropyl)pyridine (starting material D1) and 5 g of PPA (5 hours at 140° C. and chromatography using dichloromethane/methanol 30:1) give 0.151 g of the title compound of m.p. 111–113° C. The mass spectrum shows the molecular peak MH$^+$ at 311.3 Da.

13. 2-[2-(4-Methoxypyridin-2-yl)ethyl]-6-cyclohexylmethyl-3H-imidazo[4,5-b]pyridine Similarly to Example 1, 0.275 g of 3-(4-methoxypyridin-2-yl)propionic acid (starting material A1), 0.28 g of 2,3-diamino-5-cyclohexylmethylpyridine (starting material E1) and 10 g of PPA (10 hours at 145° C. and chromatography using dichloromethane/methanol 15:1) give 0.183 g of the title compound of as a brownish oil. The mass spectrum shows the molecular peak MH$^+$ at 351.4 Da.

14. 2-[2-(4-Methoxypyridin-2-yl)ethyl]-6-(2-phenyl-ethyl)-3H-imidazo[4,5-b]pyridine Similarly to Example 1, 0.69 g of 3-(4-methoxypyridin-2-yl)propionic acid (starting material A1), 0.74 g of 2,3-diamino-5-(2-phenylethyl)pyridine (starting material F1) and 12 g of PPA (24 hours at 140° C. and chromatography using dichloromethane/methanol 30:1) give 0.91 g of the title compound of m.p. 86–88° C. The mass spectrum shows the molecular peak MH$^+$ at 359.4 Da.

15. 2-[2-(4-Methoxypyridin-2-yl)ethyl]-6-(3,4-dichlorphenyl)-3H-imidazo[4,5-b]pyridine Similarly to Example 1, 0.16 g of 3-(4-methoxypyridin-2-yl)propionic acid (starting material A1), 0.74 g 2,3-diamino-5-(3,4-dichlorphenyl)pyridine (starting material G1) and 10 g of PPA (24 hours at 140° C. and chromatography using dichloromethane/methanol 18:1) give 0.12 g of the title compound of m.p. 217–218° C. The mass spectrum shows the molecular peaks MH$^+$ at 399.3 and 401.3 Da.

16. 2-[2-(4-Methoxypyridin-2-yl)ethyl]-6-(4-bromphenyl)-3H-imidazo[4,5-b]pyridine Similarly to Example 1, 0.35 g of 3-(4-methoxypyridin-2-yl)propionic acid (starting material A1), 0.425 g of 2,3-diamino-5-(4-bromphenyl)pyridine (starting material H1) and 15 g of PPA (20 hours at 135° C. and chromatography using dichloromethane/methanol 98:2+1% triethylamine) give 0.25 g of the title compound of m.p. 193–194° C. The mass spectrum shows the molecular peaks MH$^+$ at 409.3 and 411.3 Da.

17. 2-[2-(4-Methoxypyridin-2-yl)ethyl]-6-(4-brombenzyl)-3H-imidazo[4,5-b]pyridine Similarly to Example 1, 0.36 g of 3-(4-methoxypyridin-2-yl)propionic acid (starting material A1), 0.74 g of 2,3-diamino-5-(4-brombenzyl)pyridine (starting material I1) and 14 g of PPA (24 hours at 115° C. and chromatography using dichloromethane/methanol 18:2) give 0.39 g of the title compound of m.p. 169–170° C. The mass spectrum shows the molecular peak MH$^+$ at 423.3 Da.

18. 7-(2-Methoxyethoxy)-2-[2-(4-methoxypyridin-2-yl)ethyl]-3H-imidazo[4,5-b]pyridine Similarly to Example 1, 0.56 g of 3-(4-methoxypyridin-2-yl)propionic acid (starting material A1), 0.515 g of 2,3-diamino-4-(2-methoxyethoxy)pyridine (starting material j1) and 8 g of PPA (7 hours at 115°C. and chromatography using dichloromethane/methanol 18:2) give 0.21 g of the title compound of m.p. 129–131°The mass spectrum shows the molecular peak MH$^+$ at 329.2 Da.

19. 2-[2-(4-Methoxypyridin-2-yl)ethyl]-7-(2-phenylethoxy)-3H-imidazo[4,5]pyridine Similarly to Example 1, 0.374 g of 3-(4-methoxypyridin-2-yl)propionic acid (starting material A1), 0.473 g of 2,3-diamino-4-(2-phenylethoxy)pyridine (starting material K1) and 8 g of PPA (24 hours at 100° C. and chromatography using dichloromethane/methanol 18:2) give 0.097 g of the title compound as an oil, which crystallizes on standing. The mass spectrum shows the molecular peak MH$^+$ at 375.3 Da.

20. 2-[2-(4-Methoxypyridin-2-yl)ethyl]-7-(2,2,2-trifluoroethoxy)-3H-imidazo[4,5-b]pyridine Similarly to Example 1, 0.34 g of 3-(4-methoxypyridin-2-yl)propionic acid (starting material A1), 0.36 g of 2,3-diamino-4-(2,2,2-trifluoroethoxy)pyridine (starting material L1) and 6 g of PPA (7 hours at 100° C. and chromatography using dichloromethane/methanol 18:2) give 0.11 g of the title compound of m.p. 154–155° C. The mass spectrum shows the molecular peak MH$^+$ at 353.3 Da.

21. 7-Hydroxy-2-[2-(4-methoxypyridin-2-yl)ethyl]-3H-imidazo[4,5-b]pyridine

Similarly to Example 1, 0.51 g of 3-(4-methoxypyridin-2-yl)propionic acid (starting material A1), 0.49 g 2,3-diamino-4-benzyloxypyridine (starting material M1) and 6.5 g of PPA (one hour at 130° C. and chromatography using dichloromethane/methanol 18:2+1% triethylamine) give 0.19 g of the title compound of m.p. 122–124° C. The mass spectrum shows the molecular peak MH$^+$ at 271.1 Da.

22. 2-[2-(4-Methoxypyridin-2-yl)ethyl]-7-(2-p-tolyl-ethyl)-3H-imidazo[4,5-b]pyridine Similarly to Example 1, 0.53 g of 3-(4-methoxypyridin-2-yl)propionic acid (starting material A1), 0.51 g of 2,3-diamino-4-(2-p-tolylethyl)pyridine (starting material N1) and 9.0 g of PPA (24 hours at 120° C. and chromatography using dichloromethane/methanol 25:1+1% triethylamine) give 0.49 g of the title compound of m.p. 137–138° C. (crystallized from ethyl acetate/petroleum ether). The mass spectrum shows the molecular peaks MH$^+$ and 2MNa$^+$ at 373.4 and 767.1 Da.

23. 2,7-Bis-[2-(4-methoxypyridin-2-yl)ethyl]-3H-imidazo[4,5-b]pyridine

Similarly to Example 1, 0.56 g of 3-(4-methoxypyridin-2-yl)propionic acid (starting material A1), 0.58 g of 2,3-diamino-4-[2-(4-methoxypyrdin-2-yl)ethyl]pyridine (starting material O1) and 17.0 g of PPA (24 hours at 120°C. and chromatography using dichloromethane/methanol 25:1+1% triethylamine) give 0.49 g of the title compound of m.p. 137–138° C. (crystallized from ethyl acetate/petroleum ether). The mass spectrum shows the molecular peaks MH$^+$ and 2MNa$^+$ at 390.4 and 801.1 Da.

24. 2-[2-(4-Methoxypyridin-2-yl)ethyl]-7-(2-pyridin-2-yl-ethyl)-3H-imidazo[4,5-b]pyridine Similarly to Example 1, 0.544 g of 3-(4-methoxypyridin-2-yl)propionic acid (starting material A1), 0.495 g of 2,3-diamino-4-(2-pyridin-2-yl-ethyl)pyridine (starting material P1) and 15.0 g of PPA (24 hours at 120° C. and chromatography using dichloromethane/methanol 20:1+1% triethylamine) give 0.45 g of the title compound of m.p. 123–124° C. (crystallized from ethyl acetate/petroleum ether). The mass spectrum shows the molecular peaks MH$^+$ and 2MNa$^+$ at 360.3 and 740.9 Da.

25. 2-[2-(4-Methoxypyridin-2-yl)ethyl]-6-p-tolyl-3H-imidazo[4,5-b]pyridine

Similarly to Example 1, 0.52 g of 3-(4-methoxypyridin-2-yl)propionic acid (starting material A1), 0.44 g of 2,3-diamino-5-p-tolylpyridine (starting material Q1) and 10 g of PPA (24 hours at 115° C. and chromatography using dichloromethane/methanol 18:2) give 0.13 g of the title compound of m.p. 168–170° C. (from ethyl acetate/petroleum ether). The mass spectrum shows the molecular peak MH$^+$ at 345.2 Da.

26. 2-[2-(4-Methoxypyridin-2-yl)ethyl]-6-(pyridin-3-yl)-3H-imidazo-[4,5-b]pyridine Similarly to Example 1, 0.25 g of 3-(4-methoxypyridin-2-yl)propionic acid (starting material A1), 0.2 g of 2,3-diamino-5-pyridin-3-yl-pyridine (starting material R1) and 8.0 g of PPA (24 hours at 120° C. and chromatography using dichloromethane/methanol 25:1+1% triethylamine) give 0.05 g of the title compound of m.p. 107–109° C. (from ethyl acetate/petroleum ether). The mass spectrum shows the molecular peaks MH$^+$ and 2MNa$^+$ at 332.3 and 684.9 Da.

27. 2-[2-(4-Methoxypyridin-2-yl)ethyl]-6-(4-aminophenyl)-3H-imidazo-[4,5-b]pyridine 0.166 g of 2-[2-(4-methoxypyridin-2-yl)ethyl]-6-bromo-3H-imidazo[4,5-b]pyridine (example 6) and 0.13 g of 4-aminophenylboronic acid are dissolved in 8 ml of degassed dioxane. Then a solution of 0.21 g of potassium carbonate and 0.042 g of lithium chloride in 6.5 ml of degassed water and 0.058 g of tetrakis(triphenylphosphine)palladium(0) are added. The mixture is heated to reflux under N$_2$ for 24 hours and, after cooling and addition of water, it is extracted three times with dichloromethane. The combined organic phases are dried over sodium sulfate, concentrated and the residue is chromatographed on a silica gel column (dichloromethane/methanol 30–15:1). Concentration of the chromatographically pure fractions gives 0.09 g of the title compound as a yellow solid of m.p. 117–119° C. The mass spectrum shows the molecular peak MH$^+$ at 346.3 Da.

28. 2-[2-(4-Methoxypyridin-2-yl)ethyl]-6-(4-hydroxyphenyl)-3H-imidazo-[4,5-b]pyridine 0.76 g of 2-[2-(4-methoxypyridin-2-yl)ethyl]-6-iodo-3H-imidazo[4,5-b]pyridine (example 7) and 0.55 g of 4-hydroxyphenylboronic acid are dissolved in 30 ml of degassed dioxane. Then a solution of 0.55 g of potassium carbonate and 0.17 g of lithium chloride in 26 ml of degassed water and 0.23 g of tetrakis(triphenylphosphine)palladium(0) are added. The mixture is heated to reflux under N$_2$ for 56 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 30–10:1). Concentration of the chromatographically pure fractions gives 0.30 g of the title compound as a solid of m.p. 206–208° C. The mass spectrum shows the molecular peaks MH$^+$ and 2MNa$^+$ at 347.3 and 714.9 Da.

29. 2-[2-(4-Methoxypyridin-2-yl)ethyl]-6-(4-N,N-dimethylaminophenyl)-3H-imidazo[4,5-b]pyridine 0.166 g of 2-[2-(4-methoxypyridin-2-yl)ethyl]-6-bromo-3H-imidazo[4,5-b]pyridine (example 6) and 0.25 g of 4-N,N-dimethylaminophenylboronic acid are dissolved in 8 ml degassed dioxane. Then a solution of 0.138 g of potassium carbonate and 0.042 g of lithium chloride in 6.5 ml of degassed water and 0.058 g of tetrakis(triphenylphosphine)palladium(0) are added. The mixture is heated to reflux under N$_2$ for 24 hours and, after cooling and addition of water, it is extracted three times with dichloromethane. The combined organic phases are dried over sodium sulfate, concentrated and the residue is chromatographed on a silica gel column (dichloromethane/methanol 30–26:1). Concentration of the chromatographically pure fractions gives 0.17 g of the title compound as a yellow solid of m.p. 176–178° C. The mass spectrum shows the molecular peaks MH$^+$ and 2MNa$^+$ at 374.4 and 769.0 D

30. 2-[2-(4-Methoxypyridin-2-yl)ethyl]-6-(4-trifluormethylphenyl)-3H-imidazo[4,5-b]pyridine 0.166 g of 2-[2-(4-methoxypyridin-2-yl)ethyl]-6-bromo-3H-imidazo[4,5-b]pyridine (example 6) and 0.285 g of 4-trifluormethylphenylboronic acid are dissolved in 8 ml of degassed dioxane. Then a solution of 0.138 g of potassium carbonate and 0.042 g of lithium chloride in 6.5 ml of degassed water and 0.058 g of tetrakis(triphenylphosphine)palladium(0) are added. The mixture is heated to reflux under N$_2$ for 48 hours and, after cooling and addition of water, it is extracted three times with dichloromethane. The combined organic phases are dried over sodium sulfate, concentrated and the residue is chromatographed on a silica gel column (dichloromethane/methanol 30–26:1). Concentration of the chromatographically pure fractions gives 0.115 g of the title compound as a colourless solid of m.p. 191–192° C. The mass spectrum shows the molecular peak MH$^+$ at 399.4 Da.

31. 2-[2-(4-Methoxypyridin-2-yl)ethyl]-6-(3,4-dimethoxyphenyl)-3H-imidazo[4,5-b]pyridine 0.50 g of 2-[2-(4-methoxypyridin-2-yl)ethyl]-6-bromo-3H-imidazo[4,5-b]pyridine (example 6) and 0.41 g of 3,4-dimethoxyphenylboronic acid are dissolved in 25 ml of degassed dioxane. Then a solution of 0.415 g of potassium carbonate and 0.127 g of lithium chloride in 19 ml of degassed water and 0.173 g of tetrakis(triphenylphosphine)palladium(0) are added. The mixture is heated to reflux under N$_2$ for 48 hours and, after cooling and addition of water, it is extracted three times with dichloromethane. The combined organic phases are dried over sodium sulfate, concentrated and the residue is chromatographed on a silica gel column (dichloromethane/methanol 30–26:1). Concentration of the chromatographically pure fractions and crystallisation from ethyl acetate gives 0.18 g of the title compound as a yellowish solid of m.p. 185–186° C. The mass spectrum shows the molecular peaks MH$^+$ and 2MNa$^+$ at 391.3 and 803.0 Da.

32. 2-[2-(4-Methoxypyridin-2-yl)ethyl]-6-(4-benzyloxyphenyl)-3H-imidazo[4,5-b]pyridine 0.38 g of 2-[2-(4-methoxypyridin-2-yl)ethyl]-6-iodo-3H-imidazo[4,5-b]pyridine (example 7) and 0.342 g of 4-benzyloxyphenylboronic acid are dissolved in 16 ml degassed dioxane. Then a solution of 0.276 g of potassium carbonate and 0.85 g of lithium chloride in 13 ml of degassed water and 0.115 g of tetrakis(triphenylphosphine)palladium(0) are added. The mixture is heated to reflux under N$_2$ for 20 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 30–26:1). Concentration of the chromatographically pure fractions and crystallisation from ethyl acetate gives 0.28 g of the title compound as a colourless solid of m.p. 161–162° C. The mass spectrum shows the molecular peaks MH$^+$ and 2MNa$^+$ at 437.3 and 894.2 Da.

33. 2-[2-(4-Methoxypyridin-2-yl)ethyl]-(4-benzyloxy-3-fluorophenyl)-3H-imidazo[4,5-b]pyridine 0.38 g of 2-[2-(4-methoxypyridin-2-yl)ethyl]-6-iodo-3H-imidazo[4,5-b]pyridine (example 7) and 0.37 g of 4-benzyloxy-3-fluorophenylboronic acid are dissolved in 16 ml of degassed dioxane. Then a solution of 0.276 g of potassium carbonate and 0.85 g of lithium chloride in 13 ml of degassed water and 0.115 g of tetrakis(triphenylphosphine) palladium(0) are added. The mixture is heated to reflux under N$_2$ for 18 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 28:1). Concentration of the chromatographically pure fractions and crystallisation from ethyl acetate gives 0.21 g of the title compound as a yellowish solid of m.p. 168–170° C. The mass spectrum shows the molecular peak MH$^+$ at 455.3 Da.

34. 2-[2-(4-Methoxypyridin-2-yl)ethyl]-6-(4-cyanophenyl)-3H-imidazo[4,5-b]pyridine A mixture of 0.364 g of 4-bromobenzonitrile, 0.56 g of bis-(pinacolato)-diboron, 0.034 g of 1,1'-bis-(diphenylphosphino)-ferrocene, 0.044 g of [1,1'-bis(diphenylphosphino)ferrocene]palladium-di-chloride 0.588 g of potassium acetate in 20 ml of degassed dioxane are heated to reflux under N$_2$ for 16 hours. To the resulting mixture 13 ml of degassed dioxane, 0.456 g of 2-[2-(4-methoxypyridin-2-yl)ethyl]-6-iodo-3H-imidazo[4,5-b]pyridine (example 7), 0.139 g of tetrakis(triphenylphosphine)-palladium(0) and a solution of 0.332 g of potassium carbonate and 0.102 g of lithium chloride in 10 ml of degassed water are added under N$_2$. The mixture is heated to reflux under N$_2$ for 30 hours and, after cooling, addition of water and adjusting the pH to 7, it is extracted three times with dichloromethane. The combined organic phases are dried over sodium sulfate, concentrated and the residue is chromatographed on a silica gel column (dichloromethane/methanol 25–20:1). Concentration of the chromatographically pure fractions and crystallisation from ethyl acetate gives 0.2 g of the title compound as a solid of m.p. 241–242° C. The mass spectrum shows the molecular peak MH$^+$ at 356.4 Da.

35. 2-[2-(4-Methoxypyridin-2-yl)ethyl])-3H-imidazo[4,5-b]pyridine-6-carboxylic Acid Methyl Ester An autoclave (300 ml), containing 200 ml of methanol, 4.0 g of 2-[2-(4-methoxypyridin-2-yl)ethyl]-6-iodo-3H-imidazo[4,5-b]pyridine (example 7), 9.8 ml of triethylamine, 1.24 g of triphenylphosphine and 0.378 g of palladium(II) acetate is flushed with N$_2$ three times and pressurized with carbon monoxide (5 bar). The autoclave is placed in an oil bath heated at 100° C. and the whole mixture is stirred for 18 hours. After cooling the content of the autoclave is filtered, the filtrate is evaporated in vacuo and the residue is is chromatographed on a silica gel column (dichloromethane/methanol 25–20:1). Concentration of the chromatographically pure fractions and drying gives 3.3 g of the title compound as a solid of m.p. 174–176° C. The mass spectrum shows the molecular peak MH$^+$ at 313.8 Da.

36. N-(4-{2-[2-(4-Methoxypyridin-2-yl)ethyl]-3H-imidazo[4,5-b]pyridin-6-yl}phenyl)-acetamide 0.025 ml of acetic acid anhydride are added to 0.086 g of 2-[2-(4-methoxypyridin-2-yl)ethyl]-6-(4-aminophenyl)-3H-imidazo[4,5-b]pyridine (example 27) in 2 ml of dichloromethane and the mixture is stirred at ambient temperature for three hours. The solvent is evaporated in vacuo and the residue is is chromatographed on a silica gel column (dichloromethane/methanol 18:1+2% aqueous ammonia solution (25% strength)). Concentration of the chromatographically pure fractions and drying gives 0.085 g of the title compound as a solid of m.p. 220–221° C. The mass spectrum shows the molecular peaks MH$^+$ and 2MNa$^+$ at 388.4 and 797.0 Da.

37. N-(4-{2-[2-(4-Methoxypyridin-2-yl)ethyl]-3H-imidazo[4,5-b]pyridin-6-yl}phenyl)-benzenesulfonamide 0.047 ml of benzene sulfonyl chloride are added to 0.115 g of 2-[2-(4-methoxypyridin-2-yl)ethyl]-6-(4-aminophenyl)-3H-imidazo[4,5-b]pyridine (example 27) in 1 ml of pyridine and the mixture is stirred at ambient temperature for three hours. The solvent is evaporated in vacuo and the residue is is chromatographed on a silica gel column (dichloromethane/methanol 30–20:1+1% triethylamine). Concentration of the chromatographically pure fractions and drying gives 0.093 g of the title compound as a solid of m.p. 251–253° C. The mass spectrum shows the molecular peak MH$^+$ at 486.3 Da.

38. 2-[2-(4-Methoxy-1-oxy-pyridin-2-yl)ethyl])-3H-imidazo[4,5-b]pyridine

To 0.514 g of 2-[2-(4-methoxypyridin-2-yl)ethyl])-3H-imidazo[4,5-b]pyridine (example 1) dissolved in 12 ml of dichloromethane 0.523 g of 3-chloroperbenzoic acid are added at 0° C. After stirring for one hour sodium hydrogencarbonate solution is added and the organic phase is separated. The solvent is evaporated in vacuo and the residue is chromatographed on a silica gel column (dichloromethane/methanol 10–5:1). Concentration of the chromatographically pure fractions and drying gives 0.192 g of the title compound as a yellow foam. The mass spectrum shows the molecular peak MH$^+$ at 271.2 Da.

Starting Materials:

A1. 3-(4-Methoxypyridin-2-yl)propionic Acid 41.95 g of methyl 3-(4-methoxypyridin-2-yl)propionate (starting material A2) are dissolved in 700 ml of tetrahydrofuran, and 217 ml of 1N sodium hydroxide solution are added. The mixture is stirred at room temperature until no more starting material is detectable by thin-layer chromatography (TLC). The mixture is neutralized using 217 ml of 1N hydrochloric acid solution, evaporated to dryness using a rotary evaporator and dried under high vacuum. The colorless residue is ground and extracted four times with dichloromethane/methanol (9:1). The combined extracts are evaporated to dryness. This gives 33.2 g of the title compound as a colorless powder of m.p. 131–132° C. The mass spectrum shows the molecular peak MH$^+$ at 182 Da.

A2. Methyl 3-(4-methoxypyridin-2-yl)propionate 43.1 g of methyl 3-(4-methoxypyridin-2-yl)acrylate (starting material A3) in 600 ml of methanol are hydrogenated over 3.0 g of 10% strength Pd/C until the starting material has disappeared (TLC). The catalyst is filtered off, and the mixture is then concentrated and dried under high vacuum. This gives 41.95 g of the title compound as a light-yellow oil. The mass spectrum shows the molecular peak MH$^+$ at 196 Da.

A3. Methyl 3-(4-methoxypyridin-2-yl)acrylate

A mixture of 45 g of 4-methoxypyridine-2-carbaldehyde (Ashimori et al., Chem. Pharm. Bull. 38, 2446–2458 (1990)), 75.80 g of pyridine hydrochloride, 102.45 g of monomethyl malonate potassium salt and 4.1 ml of piperidine in 700 ml of pyridine are slowly heated, with stirring, to 120° C. When the evolution of gas starts, the heating source is temporarily removed to stop the reaction from becoming too violent. Once the reaction has subsided, the mixture is stirred at 120° C. for a further 2.5 h, and the pyridine is then distilled off under reduced pressure. The residue is partitioned between ethyl acetate/water and the organic phase is washed with water and dried. The residue obtained after concentration is chromatographed on a silica gel column using ethyl acetate/petroleum ether 2:1. This initially gives 43.2 g of the title compound as a yellow oil which crystallizes on standing and then shows a m.p. of 80–82° C. The mass spectrum shows the molecular peak MH$^+$ at 194 Da.

B1. 2,3-Diamino-5-trifluoromethylpyridine 0.44 g of 2-amino-3-nitro-5-trifluoromethylpyridine (starting material B2) dissolved in 50 ml methanol are hydrogenated over 0.05 g of 10% strength Pd/C until no starting material is detectable by TLC. After filtration, the solvent is evaporated and the solid residue is dried in vacuo. This gives 0.366 g of the title compound of m.p. 97–99° C. The mass spectrum shows the molecular peak MH$^+$ at 178.3 Da.

B2. 2-Amino-3-nitro-5-trifluoromethylpyridine 1.7 g of 2-triflouromethyl-1,3-bis(dimethylamino)trimethinium hexafluorophosphate (Davies et al., J. Org. Chem. 65, 4571–4574 (2000)) and 0.53 g 2-nitro-1,1-ethenediamine (Troschütz et al., Arch. Pharm. (Weinheim Ger.) 324, 73–77 (1991)) are dissolved in 48 ml of pyridine. The mixture is refluxed for 24 hours, then the solvent is removed in vacuo and after coevaporating twice with toluene the residue is partitioned between dichloromethane and water. The organic phase is dried over sodium sulfate and concentrated after filtration. The residue is chromatographed over silica gel (dichloromethane/petroleum ether 4:1+1% triethylamine). Concentration of the pure fractions and drying in vacuo gives 0.47 g of the title compound of m.p. 110–112° C. as a yellow-orange powder. The mass spectrum shows the molecular peak MH$^+$ at 208.0 Da.

C1. 2,3-Diamino-5-phenylpyridine 0.46 g of 2-amino-3-nitro-5-phenylpyridine (starting material C2) dissolved in 50 ml methanol are hydrogenated over 0.05 g of 10% strength Pd/C until no starting material is detectable by TLC. After filtration, the solvent is evaporated and the residue is chromatographed over silica gel (dichloromethane/methanol 20:1+1% triethylamine). Concentration of the pure fractions and drying in vacuo gives 0.38 g of the title compound as a brownish oil. The mass spectrum shows the molecular peak MH$^+$ at 186.2 Da.

C2. 2-Amino-3-nitro-5-phenylpyridine

Similarly to Example B2, 4.85 g of 2-phenyl-1,3-bis(dimethylamino)trimethinium perchlorate (Jutz et al., Chem. Ber. 102, 2301–2318 (1969)) and 1.65 g of 2-nitro-1,1-ethenediamine in 90 ml of pyridine give 0.67 g of the title compound of m.p. 186–188° C. (after chromatography with toluene/acetone 20:1+1% triethylamine).

D1. 2,3-Diamino-5-(2-methylpropyl)pyridine 0.46 g of 2-amino-3-nitro-5-(2-methylpropyl)pyridine (starting material D2) dissolved in 20 ml of methanol are hydrogenated over 0.05 g of 10% strength Pd/C until no starting material is detectable by TLC. After filtration, the solvent is evaporated and the residue is chromatographed over silica gel (dichloromethane/methanol 25:1). Concentration of the pure fractions and drying in vacuo gives 0.34 g of the title compound as an oil. The mass spectrum shows the molecular peak MH$^+$ at 166.2 Da.

D2. 2-Amino-3-nitro-5-(2-methylpropyl)pyridine

In a small pressure bottle 1.16 g of 2-chloro-3-nitro-5-(2-methylpropyl)pyridine (starting material D3) dissolved in 7 ml of a 5M solution of ammonia in methanol are heated to 100° C. for 10 hours. After cooling the solvent is evaporated and the residue is chromatographed over silica gel (dichloromethane/petroleum ether 5:1). Concentration of the pure fractions and drying in vacuo gives 0.49 g of the title compound as an oil, which crystallizes on standing (m.p. 147–149° C.). The mass spectrum shows the molecular peak MH$^+$ at 196.2 Da.

D3. 2-Chloro-3-nitro-5-(2-methylpropyl)pyridine

A mixture of 1.7 g of 2-hydroxy-3-nitro-5-(2-methylpropyl)pyridine (starting material D4) and 15 ml of phosphorous oxychloride is heated under reflux to 120° C. for two hours. After cooling the mixture is carefully added to ice/water, then neutralized with sodium-hydrogencarbonate and extracted three times with ethylacetate. The combined organic phases are evaporated to dryness and the residue is chromatographed on a silica gel column (ethylacetate/petroleum ether 1:15). Concentration of the chromatographically pure fractions gives 1.17 g of the title compound as an orange oil.

D4. 2-Hydroxy-3-nitro-5-(2-methylpropyl)pyridine 9.84 g of 2-(2-methylpropyl)-1,3-bis(dimethylamino)trimethinium hexafluorophosphate (prepared according to Davies et al., J. Org. Chem. 65, 4571–4574 (2000)) and 3.63 g of 2-nitroacetamide ammonium salt (Saari et al., J. Med. Chem. 35, 3792–3802 (1992)) in 50 ml of 1-propanol are heated under reflux for 24 hours. After cooling the solvent is evaporated and the residue is partitioned between ethyl acetate and water. The organic phase is dried over sodium sulfate and concentrated after filtration. The residue is chromatographed over silica gel (toluene/acetone 4:1). Concentration of the pure fractions and drying in vacuo gives 1.80 g of the title compound of m.p. 161–163° C. as a yellow powder. The mass spectrum shows the molecular peak MH$^+$ at 197 Da.

E1. 2,3-Diamino-5-cyclohexylmethylpyridine

Similiarly to Example C1, the hydrogenation of 0.365 g of 2-amino-3-nitro-5-cyclohexylmethyl-pyridine (starting material E2) gives 0.29 g of the title compound as a dark powder (after chromatography with dichloromethane/methanol 99:1). The mass spectrum shows the molecular peak MH$^+$ at 205 Da.

E2. 2-Amino-3-nitro-5-cyclohexylmethylpyridine

In a small pressure bottle 0.78 g of 2-chloro-3-nitro-5-cyclohexylmethylpyridine (starting material E3) dissolved in 7 ml of a 5M solution of ammonia in methanol are heated to 100° C. for 10 hours. On cooling in an icebath the title compound crystallizes and is isolated by suction. The mass spectrum shows the molecular peak MH$^+$ at 235.2 Da.

E3. 2-Chloro-3-nitro-5-cyclohexylmethylpyridine

A mixture of 1.8 g of 2-hydroxy-3-nitro-5-cyclohexylmethylpyridine (starting material E4) and 13 ml of phosphorous oxychloride is heated under reflux to 120° C. for two hours. After cooling the mixture is carefully added to ice/water, then neutralized with sodium hydrogencarbonate and extracted three times with ethyl acetate. The combined organic phases are evaporated to dryness and the residue is chromatographed on a silica gel column (ethylacetate/petroleum ether 1:15). Concentration of the chromatographically pure fractions gives 0.84 g of the title compound as an orange oil.

E4. 2-Hydroxy-3-nitro-5-cyclohexylmethylpyridine 11.05 g of 2-cyclohexylmethyl-1,3-bis(dimethylamino)trimethinium hexafluorophosphate (prepared according to Davies et al., J. Org. Chem. 65, 4571–4574 (2000)) and 3.63 g of 2-nitroacetamide ammonium salt (Saari et al., J. Med. Chem. 35, 3792–3802 (1992)) in 45 ml of 1-propanol are heated under reflux for 24 hours. After cooling the solvent is evaporated and the residue is partitioned between ethyl acetate and water. The organic phase is dried over sodium sulfate and concentrated after filtration. The residue is chromatographed over silica gel (toluene/acetone 4:1). Concentration of the pure fractions and drying in vacuo gives 2.22 g of the title compound as a yellow oil. The mass spectrum shows the molecular peak MH$^+$ at 237.4 Da.

F1. 2,3-Diamino-5-(2-phenylethyl)pyridine

Similiarly to Example C1, the hydrogenation of 0.92 g of 2-amino-3-nitro-5-(2-phenylethyl)-pyridine (starting material F2) gives 0.76 g of the title compound as a tan powder of m.p. 87–88° C. (after chromatography with dichloromethane/methanol 30:1). The mass spectrum shows the molecular peak MH$^+$ at 214.3 Da.

F2. 2-Amino-3-nitro-5-(2-phenylethyl)pyridine

In a small pressure bottle 1.41 g of 2-chloro-3-nitro-5-(2-phenylethyl)pyridine (starting material F3) dissolved in 8 ml of a 5M solution of ammonia in methanol are heated to 100° C. for 10 hours. On cooling in an icebath the title compound crystallizes and is isolated by suction (m.p. 145–146° C.). The mass spectrum shows the molecular peak M$^+$ at 243 Da.

F3. 2-Chloro-4-nitro-5-(2-phenylethyl)pyridine

A mixture of 3.23 g of 2-hydroxy-3-nitro-5-(2-phenylethyl)pyridine (starting material F4) and 30 ml of phosphorous oxychloride is heated under reflux to 120° C. for 2.5 hours. After cooling the mixture is carefully added to ice/water, then neutralized with sodium hydrogencarbonate and extracted three times with ethyl acetate. The combined organic phases are evaporated to dryness and the residue is chromatographed on a silica gel column (ethylacetate/petroleum ether 1:15). Concentration of the chromatographically pure fractions gives 1.42 g of the title compound as yellow crystals of m.p. 76–78° C. The mass spectrum shows the molecular peak M$^+$ at 261.1 Da.

F4. 2-Hydroxy-3-nitro-5-(2-phenylethyl)pyridine 7.53 g of 2-(2-phenylethyl)-1,3-bis(dimethylamino)trimethinium hexafluorophosphate (prepared according to Davies et al., J. Org. Chem. 65, 4571–4574 (2000)) and 2.42 g of 2-nitroacetamide ammonium salt (Saari et al., J. Med. Chem. 35, 3792–3802 (1992)) in 20 ml of 1-propanol are heated under reflux for 24 hours. After cooling the solvent is evaporated and the residue is partitioned between ethyl acetate and water. The organic phase is dried over sodium sulfate and concentrated after filtration. The residue is chromatographed over silica gel (toluene/acetone 4:1). Concentration of the pure fractions and drying in vacuo gives 1.08 g of the title compound as a yellow oil. The mass spectrum shows the molecular peak MH$^+$ at 245.3 Da.

G1. 2,3-Diamino-5-(3,4-dichlorphenyl)pyridine 0.051 g of ferric chloride and 0.085 g of activated charcoal are added to a suspension of 0.35 g of 2-amino-5-(3,4-dichlorphenyl)-3-nitropyridine (starting material G2) in 10 ml of methanol and the mixture is heated under reflux. 0.270 ml of hydrazine hydrate are added slowly and reflux is continued for 12 hours. After cooling the mixture is filtered and the filtrate is evaporated. The residue is partitioned between sodium-EDTA-solution (0.25M; pH 9–10) and dichloromethane. The organic phase is evaporated to give 0.20 g of the title compound as a yellowish solid of m.p. 202–204° C. The mass spectrum shows the molecular peak MH$^+$ at 254.2 Da.

G2. 2-Amino-5-(3,4-dichlorphenyl)-3-nitropyridine

Similiarly to Example F2, 0.865 g of 2-chloro-5-(3,4-dichlorphenyl)-3-nitropyridine (starting material G3) and 5 ml of a 5M solution of ammonia in methanol give 0.63 g of the title compound as yellow crystals of m.p. 256–257° C. The mass spectrum shows the molecular peak MH$^+$ at 284.0 Da.

G3. 2-Chloro-5-(3,4-dichlorphenyl)-3-nitropyridine

A mixture of 1.6 g of 5-(3,4-dichlorphenyl)-2-hydroxy-3-nitropyridine (starting material G4) and 10 ml of phosphorous oxychloride is heated under reflux to 120° C. for 3 hours. After cooling the mixture is carefully added to ice/water, then neutralized with sodium hydrogencarbonate and extracted three times with ethyl acetate. The combined organic phases are evaporated to dryness and the residue is chromatographed on a silica gel column (ethylacetate/petroleum ether 1:20). Concentration of the chromatographically pure fractions gives 0.88 g of the title compound as yellow crystals. The mass spectrum shows the molecular peak M⁺ at 302 Da.

G4.
5-(3,4-Dichlorphenyl)-2-hydroxy-3-nitropyridine 12.5 g of 2-(3,4-dichlorphenyl)-1,3-bis(dimethylamino) trimethinium hexafluorophosphate (prepared according to Davies et al., J. Org. Chem. 65, 4571–4574 (2000)) and 3.63 g of 2-nitroacetamide ammonium salt (Saari et al., J. Med. Chem. 35, 3792–3802 (1992)) In 50 ml of 1-propanol are heated under reflux for 24 hours. After cooling the solvent is evaporated and the residue is partitioned between ethyl acetate and water. The organic phase is dried over sodium sulfate and concentrated after filtration. The residue is chromatographed over silica gel (toluene/acetone 4:1). Concentration of the pure fractions and drying in vacuo gives 1.7 g of the title compound as a yellow-orange solid. The mass spectrum shows the molecular peak M⁺ at 284 Da.

H1. 2,3-Diamino-5-(4-bromphenyl)pyridine 0.145 g of ferric chloride and 0.12 g of activated charcoal are added to a suspension of 0.98 g of 2-amino-5-(4-bromphenyl)-3-nitropyridine (starting material H2) in 30 ml of methanol and the mixture is heated under reflux. 0.725 ml of hydrazine hydrate are added slowly and reflux is continued for 24 hours. After cooling the mixture is filtered and the filtrate is evaporated. The residue is partitioned between sodium-EDTA-solution (0.25M; pH 9–10) and dichloromethane. The organic phase is evaporated to give 0.45 g of the title compound as a yellowish solid of m.p. 187–188° C. The mass spectrum shows the molecular peak MH⁺ at 264.2 Da.

H2. 2-Amino-5-(4-bromphenyl)-3-nitropyridine

Similiarly to Example F2, 1.48 g of 2-chloro-5-(4-bromphenyl)-3-nitropyridine (starting material H3) and 12 ml of a 5M solution of ammonia in methanol give 1.08 g of the title compound as orange crystals of m.p. 210–211° C. The mass spectrum shows the molecular peak M⁺ at 293.1 Da.

H3. 2-Chloro-5-(4-bromphenyl)-3-nitropyridine

A mixture of 10.2 g of 5-(4-bromphenyl)-2-hydroxy-3-nitropyridine (starting material H4) and 40 ml of phosphorous oxychloride is heated under reflux to 120° C. for 3 hours. After cooling the mixture is carefully added to ice/water, then neutralized with sodium hydrogencarbonate and extracted three times with ethyl acetate. The combined organic phases are evaporated to dryness and the residue is chromatographed on a silica gel column (ethyl acetate/ petroleum ether 1:12). Concentration of the chromatographically pure fractions gives 1.52 g of the title compound as yellow crystals of m.p. 116–117° C. The mass spectrum shows the molecular peak M⁺ at 314 Da.

H4. 5-(4-Bromphenyl)-2-hydroxy-3-nitropyridine 25.62 g of 2-(4-bromphenyl)-1,3-bis(dimethylamino)trimethinium hexafluorophosphate (prepared according to Davies et al., J. Org. Chem. 65, 4571–4574 (2000)) and 7.27 g of 2-nitroacetamide ammonium salt (Saari et al., J. Med. Chem. 35, 3792–3802 (1992)) in 60 ml of 1-propanol are heated under reflux for 24 hours. After cooling the solvent is evaporated and the residue is partitioned between ethyl acetate and water. The organic phase is dried over sodium sulfate and concentrated after filtration. The residue is chromatographed over silica gel (toluene/acetone 5:1). Concentration of the pure fractions and drying in vacuo gives 10.3 g of the title compound as a yellow-orange solid of m.p. 103–105° C. The mass spectrum shows the molecular peak M⁺ at 294 Da.

11. 2,3-Diamino-5-(4-brombenzyl)pyridine 0.012 g of ferric chloride and 0.02 g of activated charcoal are added to a suspension of 0.86 g of 2-amino-5-(4-brombenzyl)-3-nitropyridine (starting material 12) in 25 ml of methanol and the mixture is heated under reflux. 0.5 ml of hydrazine hydrate are added slowly and reflux is continued for 24 hours. After cooling the mixture is filtered and the filtrate is evaporated. The residue is partitioned between sodium-EDTA-solution (0.25M; pH 9–10) and dichloromethane. The organic phase is evaporated to give 0.67 g of the title compound. The mass spectrum shows the molecular peaks MH⁺ at 278.2 and 280.2 Da.

12. 2-Amino-5-(4-brombenzyl)-3-nitropyridine

Similarly to Example F2, 1.2 g of 2-chloro-5-(4-brombenzyl)-3-nitropyridine (starting material 13) and 10 ml of a 5M solution of ammonia in methanol give 0.86 g of the title compound as orange crystals. The mass spectrum shows the molecular peak M⁺ at 308 Da.

13. 2-Chloro-5-(4-brombenzyl)-3-nitropyridine

A mixture of 9.7 g of 5-(4-brombenzyl)-2-hydroxy-3-nitropyridine (starting material 14) and 30 ml of phosphorous oxychloride is heated under reflux to 120° C. for 3 hours. After cooling the mixture is carefully added to ice/water, then neutralized with sodium hydrogencarbonate and extracted three times with ethyl acetate. The combined organic phases are evaporated to dryness and the residue is chromatographed on a silica gel column (ethyl acetate/ petroleum ether 1:10). Concentration of the chromatographically pure fractions gives 1.4 g of the title compound as yellow crystals of m.p. 94–96° C. The mass spectrum shows the molecular peak M⁺ at 327 Da.

14. 544-Brombenzyl)-2-hydroxy-3-nitropyridine 20.5 g of 2-(4-brombenzyl)-1,3-bis(dimethylamino)trimethinium hexafluorophosphate (prepared according to Davies et al., J. Org. Chem. 65, 4571–4574 (2000)) and 5.63 g of 2-nitroacetamide ammonium salt (Saari et al., J. Med. Chem. 35, 3792–3802 (1992)) in 80 ml of 1-propanol are heated under reflux for 7 hours. After cooling the solvent is evaporated and the residue is partitioned between ethyl acetate and water. The organic phase is dried over sodium sulfate and concentrated after filtration. The residue is chromatographed over silica gel (toluene/acetone 4:1). Concentration of the pure fractions and drying in vacuo gives 9.8 g of the title compound as a yellow-orange solid. The mass spectrum shows the molecular peak M⁺ at 307.1 Da.

J1. 2,3-Diamino-4-(2-methoxyethoxy)pyridine 1.87 g of 2-benzylamino-4-(2-methoxyethoxy)-3-nitropyridine (starting material J2) are dissolved in a mixture of 30 ml of methanol and 6.16 ml of 2N aqueous hydrochloric acid and hydrogenated over 500 mg of 10% strength Pd on carbon at 50° C. for 5 hours. After filtration and addition of 6.16 ml of 2N aqueous sodium hydroxide solution the mixture is evaporated to dryness and the residue is chromatographed on silica gel (dichloromethane/methanol 25:1+ 1% triethylamine). Concentration of the pure fractions and drying in vacuo gives 0.89 g of the title compound as a brownish oil. The mass spectrum shows the molecular peak $M^+$ at 184.0 Da.

J2. 2-Benzylamino-4-(2-methoxyethoxy)-3-nitropyridine 2.32 g of 2-fluoro-4-(2-methoxyethoxy)-3-nitropyridine (starting material J3), 4.44 g of potassium carbonate and 1.11 ml of benzylamine in 25 ml of N-methylpyrrolidone are stirred at room temperature for 5 hours. The mixture is diluted with water and then extracted twice with diethylether. The combined ether phases are washed with with water and brine and are then concentrated in vacuo. The residue is chromatographed on silica gel (ethyl acetate/ petroleum ether 1:2). Concentration of the pure fractions and drying in vacuo gives 2.0 g of the title compound as a yellow oil, which crystallizes on standing (m.p. 81–83° C.). The mass spectrum shows the molecular peak $MH^+$ at 304.0 Da.

J3. 2-Fluoro-4-(2-methoxyethoxy)-3-nitropyridine

A solution of sodium 2-methoxyethanolate is prepared by adding 1.00 ml 2-methoxyethanol to a suspension of 0.416 g sodium hydride (80% strength) in 10 ml tetrahydrofurane (THF). This solution is added slowly to 2.02 g of 1,4-difluoro-3-nitropyridine (Sledeski et al.; J. Org. Chem. 65, 8114–8118 (2000)) dissolved in 60 ml of tetrahydrofurane at 0° C. Stirring at the same temperature is continued for 0.5 hours, then water is added and the mixture is evaporated to dryness in vacuo. The residue is partitioned between ethyl acetate and water and, after drying over sodium sulfate, the organic phase is concentrated and the residue is dried in vacuo. This gives 2.32 g of the title compound as a yellow oil, which is used in the next step without further purification. The mass spectrum shows the molecular peak $MH^+$ at 217.0 Da.

K1. 2,3-Diamino-4-(2-phenylethoxy)pyridine

A mixture of 1.11 g of 2-amino-4-(2-phenylethoxy)-3-nitropyridine (starting material K2), 1.0 ml of hydrazine hydrate and 0.130 g of Raney nickel in 30 ml of methanol is heated under reflux until no starting material is detectable by TLC. After filtration and evaporation of the solvent the residue is chromatographed on silica gel (dichloromethane/methanol 20:1+1% triethylamine). Concentration of the pure fractions and drying in vacuo gives 0.68 g of the title compound as an oil, which crystallizes on standing (m.p. 86–87° C.). The mass spectrum shows the molecular peak $MH^+$ at 230.2 Da.

K2. 2-Amino-4-(2-phenylethoxy)-3-nitropyridine 2.02 g of 2-fluoro-4-(2-phenylethoxy)-3-nitropyridine (starting material K3) are dissolved in 10 ml of a 5M solution of ammonia in methanol and stirred at ambient temperature for 16 hours. The solvent is distilled off and the residue is chromatographed on silica gel (dichloromethane/ petroleum ether 4:1+1% triethylamine). Concentration of the pure fractions and drying in vacuo gives 1.16 g of the title compound as a yellow solid of m.p. 131–132° C. The mass spectrum shows the molecular peak $MH^+$ at 260.0 Da.

K3. 2-Fluoro-4-(2-phenylethoxy)-3-nitropyridine

Similiarly to Example J3., 1.57 g of 2,4-difluoro-3-nitropyridine, 1.15 ml of 2-phenylethanol and 0.324 g of sodium hydride (80% strength) give 2.02 g of the title compound as an yellow oil which is used in the next step without further purification.

L1. 2,3-Diamino-4-(2,2,2-trifluoroethoxy)pyridine 2.51 g of 2-benzylamino-3-nitro-4-(2,2,2-trifluoroyethoxy)pyridine (starting material L2) are dissolved in a mixture of 50 ml of methanol and 7.66 ml of 2N aqueous hydrochloric acid and hydrogenated over 500 mg of 10% strength palladium on carbon at 50° C. for 8 hours. After filtration and addition of 7.66 ml of 2N aqueous sodium hydroxide solution the mixture is evaporated to dryness and the residue is chromatographed on silica gel (dichloromethane/methanol 20:1+1% triethylamine). Concentration of the pure fractions and drying in vacuo gives 0.43 g of the title compound as brownish crystals of m.p. 126–128° C. The mass spectrum shows the molecular peak $MH^+$ at 208.2 Da.

L2. 2-Benzylamino-3-nitro-4-(2,2,2-trifluoroyethoxy)pyridine 2.32 g of 2-fluoro-3-nitro-4-(2,2,2-trifluoroethoxy)pyridine (starting material L3), 5.52 g of potassium carbonate and 1.38 ml of benzylamine in 30 ml of N-methylpyrrolidone are stirred at room temperature for 5 hours. The mixture is diluted with water and then extracted twice with diethylether. The combined ether phases are washed with with water and brine and are then concentrated in vacuo. The residue is chromatographed on silica gel (ethyl acetate/ petroleum ether 1:5). Concentration of the pure fractions and drying in vacuo gives 2.65 g of the title compound as a yellow oil, which crystallizes on standing (m.p. 71–73° C.). The mass spectrum shows the molecular peak $MH^+$ at 328.0 Da.

L3. 2-Fluoro-3-nitro-4-(2,2,2-trifluoroethoxy)pyridine

Similiarly to Example J3., 1.57 g of 2,4-difluoro-3-nitropyridine, 1.15 ml of 2-phenylethanol and 0.324 g of sodium hydride (80% strength) give 2.02 g of the title compound as an yellow oil which is used in the next step without further purification. The mass spectrum shows the molecular peak $MH^+$ at 241.0 Da.

M1. 2,3-Diamino-4-benzyloxypyridine

A mixture of 0.88 g of 2-amino-4-benzyloxy-3-nitropyridine (starting material M2), 0.81 ml of hydrazine hydrate and 0.100 g of Raney nickel in 25 ml of methanol is heated under reflux until no starting material is detectable by TLC. After filtration and evaporation of the solvent the residue is chromatographed on silica gel (dichloromethane/methanol 20:1+1% triethylamine). Concentration of the pure fractions and drying in vacuo gives 0.66 g of the title compound as a brownish solid of m.p. 135–136° C. The mass spectrum shows the molecular peak MH$^+$ at 216.1 Da.

M2. 2-Amino-4-benzyloxy-3-nitropyridine 0.73 g of 4-benzyloxy-2-fluoro-3-nitropyridine (starting material M3) are dissolved in 10 ml of a 5M solution of ammonia in methanol and stirred at ambient temperature for 16 hours. The solvent is distilled off and the residue is chromatographed on silica gel (dichloromethane/petroleum ether 4:1+1% triethylamine). Concentration of the pure fractions and drying in vacuo gives 0.51 g of the title compound as a yellow solid of m.p. 145–147° C. The mass spectrum shows the molecular peak MH$^+$ at 246.0 Da.

M3. 4-Benzyloxy-2-fluoro-3-nitropyridine

Similiarly to Example J3., 1.5 g of 2,4-difluoro-3-nitropyridine, 0.97 ml of benzylalcohol and 0.309 g of sodium hydride (80% strength) give 0.69 g of the title compound as an yellow solid (m.p. 96–98° C.) which is used in the next step without further purification. The mass spectrum shows the molecular peak MH$^+$ at 249.0 Da.

N1. 2,3-Diamino-4-(2-p-tolyl-ethyl)pyridine 1.52 g of 2-amino-4-(2-p-tolyl-ethenyl)-3-nitropyridine (starting material N2) are dissolved in 30 ml of methanol and, after addition of 0.25 g of 10% strength palladium on carbon, are hydrogenated at 45° C. for 17 hours. The catalyst is filtered off, the filtrate is evaporated to dryness and the residue is chromatographed on a silica gel column (dichloromethane/methanol 25:1+1% triethylamine). Concentration of the pure fractions and drying in vacuo gives 0.80 g of the title compound as a brownish solid of m.p. 119–121° C. The mass spectrum shows the molecular peak MH$^+$ at 228.2 Da.

N2. 2-Amino-4-(2-p-tolyl-ethenyl)-3-nitropyridine

A mixture of 2.0 g of 2-amino-4-methyl-3-nitropyridine, 1.54 ml of 4-methylbenzaldehyde and 0.4 ml of piperidine is heated to 170° C. with stirring for 1.5 hours. After cooling to about 60–70° C. 20 ml of methanol are added and, after further cooling, the yellow precipitate formed is isolated by suction. This gives 1.67 g of the title compound of m.p. 142–146° C. The mass spectrum shows the molecular peak MH$^+$ at 256.2 Da.

O1. 2,3-Diamino-4-[2-(4-methoxypyridin-2-yl)ethyl]pyridine

Similarly to Example N1, 2.14 g of 2-amino-4-[2-(4-methoxypyridin-2-yl)ethenyl]-3-nitropyridine (starting material O2) are hydrogenated to give 1.77 g of the title compound of m.p. 89–91° C. The mass spectrum shows the molecular peak MH$^+$ at 245.3 Da.

O2. 2-Amino-4-[2-(4-methoxypyridin-2-yl)ethenyl]-3-nitropyridine

Similarly to Example N2, the condensation of 2.58 g of 2-amino-4-methyl-3-nitropyridine and 2.26 g of 4-methoxypyridine-2-carbaldehyde (Ashimori et al., Chem. Pharm. Bull. 38, 2446–2458 (1990) gives 3.28 g of the title compound of m.p. 170–172° C. The mass spectrum shows the molecular peak MH$^+$ at 273.0 Da.

P1. 2,3-Diamino-4-(2-pyridin-2-yl-ethyl)pyridine

Similarly to Example N1, 1.85 g of 2-amino-4-(2-pyridin-2-yl-ethenyl)-3-nitropyridine (starting material P2) are hydrogenated to give 1.34 g of the title compound as a brownish oil. The mass spectrum shows the molecular peak MH$^+$ at 215.2 Da.

P2. 2-Amino-4-(2-pyridin-2-yl-ethenyl)-3-nitropyridine

Similarly to Example N2, the condensation of 2.58 g of 2-amino-4-methyl-3-nitropyridine and 1.8 g of pyridine-2-carbaldehyde gives 2.03 g of the title compound of m.p. 161–163° C. The mass spectrum shows the molecular peak MH$^+$ at 243.0 Da.

Q1. 2,3-Diamino-5-p-tolylpyridine

Similarly to Example C1, the hydrogenation of 0.66 g of 2-amino-3-nitro-5-p-tolylpyridine (starting material Q2) gives 0.45 g of the title compound as a brownish oil (after chromatography with dichloromethane/methanol 24:1+1% triethylamine). The mass spectrum shows the molecular peak MH$^+$ at 200.2 Da.

Q2. 2-Amino-3-nitro-5-p-tolylpyridine 0.19 g of dichlorobis(tricyclohexylphosphine)palladium, 0.754 g of 4-tolyl-boronic acid and 12.5 ml of a 2N sodium carbonate solution are added to a solution of 0.93 g of 2-amino-5-bromo-3-nitropyridine in 20 ml of degassed dioxane. The mixture is heated to reflux under N$_2$ for 2.5 hours and, after cooling and addition of water, extracted three times with dichloromethane. The combined organic phases are dried over sodium sulfate and concentrated until a solid begins to precipitate. After addition of petroleum ether, the orange solid is isolated by suction, washed with petroleum ether and dried in vacuo. This gives 0.73 g of the title compound of m.p. 183–184° C. The mass spectrum shows the molecular peak MH$^+$ at 230.1 Da.

R1. 2,3-Diamino-5-pyridin-3-yl-pyridine

Similarly to Example C1, the hydrogenation of 0.51 g of 2-amino-3-nitro-5-pyridin-3-yl-pyridine (starting material R2) gives 0.22 g of the title compound as a brownish oil (after chromatography with dichloromethane/methanol 24:1+1% triethylamine) which crystallizes on standing (m.p. 122–124° C.). The mass spectrum shows the molecular peak MH$^+$ at 187.0 Da.

R2. 2-Amino-3-nitro-5-pyridin-3-yl-pyridine 0.21 g of dichlorobis(tricyclohexylphosphine)palladium, 0.66 g of 3-pyridyl-boronic acid and 14 ml of a 2N sodium carbonate solution are added to a solution of 1.02 g of 2-amino-5-bromo-3-nitropyridine in 40 ml of degassed dioxane. The mixture is heated to reflux under N$_2$ for 28 hours and, after cooling and addition of water, extracted three times with dichloromethane. The combined organic phases are dried over sodium sulfate, concentrated and the residue is crystallized from ethyl acetate. This gives 0.58 g of the title compound of m.p. 226–228° C. The mass spectrum shows the molecular peak MH⁺ at 217.2 Da.

Commercial Applicability

The compounds according to the invention have valuable pharmacological properties which make them commercially utilizable. They are selective inhibitors of the enzyme inducible nitric oxide synthase. Nitric oxide synthases (NO-syntases, NOSs) are enzymes that generate NO and citrulline from the amino acid arginine. In certain pathophysiological situations such as arginine depletion or tetrahydrobiopterin depletion the generation of $O_2^-$ from NO-synthases instead or together with NO has been reported. NO is long known as a signalling molecule in most living organisms including mammals and humans. The most prominent action of NO is it's smooth muscle relaxing activity, which is caused on the molecular level by the activation of soluble guanylate cyclase. In the last years a lot of other enzymes have been shown to be regulated by NO or reaction products of NO.

There exist three isoforms of NO-synthases which fall into two classes and differ in their physiologic functions and molecular properties. The first class, known as constitutive NO-synthases, comprises of the endothelial NO-synthase and the neuronal NO-synthase. Both isoenzymes are expressed constitutively in various cell types, but are most prominent in endothelial cells of blood vessel walls (therefore called endothelial NO-synthase, eNOS or NOS-III) and in neuronal cells (therefore called neuronal NO-synthase, nNOS or NOS-1). Activation of these two enzymes is dependent on $Ca^{2+}$/Calmodulin which is generated by transient increases of the intracellular free $Ca^{2+}$ concentration. Activation of constitutive isoforms leads to transient bursts of nitric oxide resulting in nanomolar cellular or tissue NO concentrations. The endothelial isoform is involved in the physiologic regulation of blood pressure. NO generated by the neuronal isoform seems to have neurotransmitter function and the neuronal isoform is among other regulatory processes involved in memory function (long term potentiation).

In contrast to the constitutive isoforms the activation of inducible NO-synthase (iNOS, NOS-II), the sole member of the second class, is performed by transcriptional activation of the iNOS-promoter. Proinflammatory stimuli lead to transcription of the gene for inducible NO-synthase, which is catalytically active without increases in the intracellular $Ca^{2+}$-concentration. Due to the long half live of the inducible NO-synthase and the unregulated activity of the enzyme, high micromolar concentrations of NO are generated over longer time periods. These high NO-concentrations alone or in cooperation with other reactive radicals such as $O_2^-$ are cytotoxic. Therefore, in situations of microbial infections, iNOS is involved in cell killing by macrophages and other immune cells during early nonspecific immune responses.

There are a number of pathophysiological situations which among others are characterized by the high expression of inducible NO-synthase and concomitant high NO or $O_2^-$ concentrations. It has been shown that these high NO concentrations alone or in combination with other radical species lead to tissue and organ damage and are causally involved in these pathophysiologies. As inflammation is characterized by the expression of proinflammatory enzymes, including inducible NO-synthase, acute and chronical inflammatory processes are promising diseases for the therapeutic application of selective inhibitors of inducible NO-synthase. Other pathophysiologies with high NO-production from inducible NO-synthase are several forms of shock (septic, hemorrhagic and cytokine-induced). It is clear that nonselective NO-synthase inhibitors will lead to cardiovascular and neuronal side effects due to concomitant inhibition of constitutive NO-synthase isoforms.

It has been shown in in-vivo animal models of septic shock that reduction of circulating plasma NO-levels by NO-scavenger or inhibition of inducible NO-synthase restores systemic blood pressure, reduces organ damage and increases survival (deangelo Exp. Opin. Pharmacother. 19–29, 1999; Redl et al. Shock 8, Suppl. 51, 1997; Strand et al. Crit. Care Med. 26, 1490–1499, 1998). It has also been shown that increased NO production during septic shock contributes to cardiac depression and myocardial dysfunction (Sun et al. J. Mol. Cell Cardiol. 30, 989–997, 1998). Furthermore there are also reports showing reduced infarct size after occlusion of the left anterior coronary artery in the presence of NO-synthase inhibitors (Wang et al. Am. J. Hyperttens. 12, 174–182, 1999). Considerable inducible NO-synthase activity is found in human cardiomyopathy and myocarditis, supporting the hypothesis that NO accounts at least in part for the dilatation and impaired contractility in these pathophysiologies (de Belder et al. Br. Heart. J. 4, 426–430, 1995).

In animal models of acute or chronic inflammation, blockade of inducible NO-synthase by isoform-selective or nonselective inhibitors or genetic knock out improves therapeutic outcome. It is reported that experimental arthritis (Connor et al. Eur. J. Pharmacol. 273, 15–24, 1995) and osteoarthritis (Pelletier et al. Arthritis & Rheum. 41, 1275–1286, 1998), experimental inflammations of the gastrointestinal tract (Zingarelli et al. Gut 45, 199–209, 1999), experimental glomerulonephritis (Narita et al. Lab. Invest. 72, 17–24, 1995), experimental diabetes (Corbett et al. PNAS 90, 8992–8995, 1993), LPS-induced experimental lung injury is reduced by inhibition of inducible NO-synthase or in iNOS-knock out mice (Kristof et al. Am. J. Crit. Care. Med. 158, 1883–1889, 1998). A pathophysiological role of inducible NO-synthase derived NO or $O_2^-$ is also discussed in chronic inflammatory diseases such as asthma, bronchitis and COPD.

Furthermore, in models of neurodegenerative diseases of the CNS such as MPTP-induced parkinsonism, amyloid peptide induced Alzheimer's disease (Ishii et al., FASEB J. 14, 1485–1489, 2000), malonate induced Huntington's disease (Connop et al. Neuropharmacol. 35, 459–465, 1996), experimental menengitis (Korytko & Boje Neuropharmacol. 35, 231–237, 1996) and experimental encephalitis (Parkinson et al. J. Mol. Med. 75, 174–186, 1997) a causal participation of NO and inducible NO-synthase has been shown.

Increased iNOS expression has been found in the brains of AIDS victims and it is reasonable to assume a role of iNOS in AIDS related dementia (Bagasra et al. J. Neurovirol. 3 153–167, 1997).

Other studies implicated nitric oxide as a potential mediator of microglia dependent primary demyelination, a hallmark of multiple sclerosis (Parkinson et al. J. Mol. Med. 75, 174–186, 1997).

An inflammatory reaction with concomitant expression of inducible NO-synthase also takes place during cerebral ischemia and reperfusion (Iadecola et al. Stroke 27, 1373–1380, 1996). Resulting NO together with $O_2^-$ from infiltrating neutrophils is thought to be responsible for cellular and organ damage. Also, in models of traumatic brain injury (Mesenge et al. J. Neurotrauma 13, 209–214, 1996; Wada et al. Neurosurgery 43, 1427–1436, 1998) NO-synthase inhibitors have been show to posses protective properties. A regulatory role for inducible NO-synthase has been reported in various tumor cell lines (Tozer & Everett Clin Oncol. 9.357–264, 1997).

On account of their inducible NO-synthase-inhibiting properties, the compounds according to the invention can be employed in human and veterinary medicine and therapeutics, where an excess of NO or $O_2^-$ due to increases in the activity of inducible NO-synthase is involved. They can be used without limitation for the treatment and prophylaxis of the following diseases:

Acute inflammatory diseases: Septic shock, sepsis, SIRS, hemorrhagic shock, shock states induced by cytokine therapy (IL-2, TNF), organ transplantation and transplant rejection, head trauma, acute lung injury, ARDS, inflammatory skin conditions such as sunburn, inflammatory eye conditions such as uveitis, glaucoma and conjunctivitis.

Chronic inflammatory diseases of peripheral organs and the CNS: gastrointestinal inflammatory diseases such as Crohn's disease, inflammatory bowel disease, ulcerative colitis, lung inflammatory diseases such as asthma and COPD, arthritic disorders such as rheumatoid arthritis, osteoarthritis and gouty arthritis, heart disorders such as cardiomyopathy and myocarditis, artherosclerosis, neurogenic inflammation, skin diseases such as psoriasis, dermatitis and eczema, diabetes, glomerulonephritis; dementias such as dementias of the Alzheimer's type, vascular dementia, dementia due to a general medical condition, such as AIDS-, Parkinson's disease, Huntington's induced dementias, ALS, multiple sklerosis; necrotizing vasculitides such as polyarteritis nodosa, serum sickness, Wegener's granulomatosis, Kawasaki's syndrome; headaches such as migraine, chronic tension headaches, cluster and vascular headaches, post-traumatic stress disorders; pain disorders such as neuropathic pain; myocardial and cerebral ischemia/reperfusion injury.

The compounds may also be useful in the treatment of cancers that express nitric oxide synthase.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention furthermore relates to pharmaceutical compositions for the treatment and/or prophylaxis of the illnesses mentioned, which contain one or more of the compounds according to the invention.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantagously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®), Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for iNOS inhibitors. Topical application forms (such as ointments) for the treatment of dermatoses thus contain the active compounds in a concentration of, for example, 0.1–99%. The dose for administration by inhalation is customarily between 0.1 and 10 mg per day. The customary dose in the case of systemic therapy (p.o.) is between 0.3 and 30 mg/kg per day, (i. v.) is between 0.3 and 30 mg/kg/h.

Biological Investigations

Measurement of Inducible NO-Synthase Activity

The assay is performed in 96-well microtiter F-plates (Greiner, Frickenhausen, FRG) in a total volume of 100 µl in the presence of 100 nM calmodulin, 226 µM $CaCl_2$, 477 µM $MgCl_2$, 5 µM flavin-adenine-dinucleotide (FAD), 5 µM flavin mononucleotide (FMN), 0.1 mM NADPH, 7 mM glutathione, 10 µM BH4 and 100 mM HEPES pH 7.2. Arginine concentrations are 0.1 µM for enzyme inhibition experiments. 150000 dpm of [$^3$H]arginine are added to the assay mixture. Enzyme reaction is started by the addition of 4 µg of a crude cytosolic fraction containing human inducible NO-synthase and the reaction mixture is incubated for 45 to 60 min at 37° C. Enzyme reaction is stopped by adding 10 µl of 2M MES-buffer pH 5.0. 50 µl of the incubation mixture are transferred into a MADP N65 filtration microtiter plate (Millipore, Eschborn, FRG) containing already 50 µl of AG-50W-X8 cation exchange resin (Biorad, München, FRG). The resin in the Na loaded form is pre-equilibrated in water and 70 µl (corresponding to 50 µl dry beads) are pipetted under heavy stirring with a 8 channel pipette into the filtration plate. After pipetting 50 µl of the enzyme reaction mixture onto the filtration plates, the plates are placed on a filtration manifold (Porvair, Shepperton, UK) and the flow through is collected in Pico scintillation plates (Packard, Meriden, Conn.). The resin in the filtration plates is washed with 75 µl of water (1×50 µl and 1×25 µl) which is also collected in the same plate as the sample. The total flow through of 125 µl is mixed with 175 µl of Microscint-40 scintillation cocktail (Packard) and the scintillation plate is sealed with TopSeal P-foil (Packard). Scintillation plates are counted in a szintillation counter.

For the measurement of inducible NO-synthase-inhibiting potencies of compounds increasing concentrations of inhibitors were included into the incubation mixture. $IC_{50}$-values were calculated from the percent inhibition at given concentrations by nonlinear least square fitting.

The inhibitory values determined for the compounds according to the invention follow from the following table A, in which the compound numbers correspond to the example numbers.

TABLE A

| Inhibition of iNOS activity [measured as $-logIC_{50}$ (mol/l)] | |
|---|---|
| compound | $-logIC_{50}$ |
| 1 | 7.03 |
| 7 | 7.49 |
| 9 | 7.05 |
| 10 | 7.41 |
| 11 | 7.16 |
| 14 | 7.34 |
| 15 | 7.33 |
| 16 | 7.36 |
| 25 | 7.46 |
| 26 | 7.05 |
| 27 | 7.21 |
| 28 | 7.35 |
| 29 | 7.42 |
| 30 | 7.55 |
| 31 | 7.12 |
| 32 | 7.34 |

TABLE A-continued

| Inhibition of iNOS activity [measured as $-logIC_{50}$ (mol/l)] | |
|---|---|
| compound | $-logIC_{50}$ |
| 33 | 7.29 |
| 34 | 7.47 |
| 36 | 7.17 |
| 37 | 7.20 |

The invention claimed is:

1. A compound of formula I

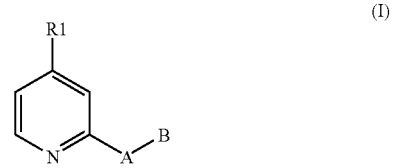

in which
R1 is 1–4C-alkoxy,
A is 1–4C-alkylene,
B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where
R2 is halogen, hydroxyl, nitro, amino, 1–7C-alkyl, trifluoromethyl, 3–7C-cycloalkyl, 3–7C-cycloalkyl-1–4C-alkyl, 1–4C-alkoxy, 1–4C-alkoxy which is completely or predominantly substituted by fluorine, 1–4C-alkoxy-1–4C-alkyl, 1–4C-alkoxy-1–4C-alkoxy, 1–4C-alkoxycarbonyl, mono- or di-1–4C-alkylaminocarbonyl, mono- or di-1–4C-alkylaminosulfonyl, 1–4C-alkylcarbonylamino, 1–4C-alkylsulfonylamino, phenyl, phenyl substituted by R21 and/or R211, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where
R21 is cyano, halogen, carboxyl, 1–4C-alkyl, 1–4C-alkoxy, aminocarbonyl, mono- or di-1–4C-alkylaminocarbonyl, 1–4C-alkylcarbonylamino, 1–4C-alkoxycarbonyl, aminosulfonyl, mono- or di-1–4C-alkylaminosulfonyl, amino, mono- or di-1–4C-alkylamino, trifluoromethyl, hydroxyl, phenylsulfonylamino or phenyl-1–4C-alkoxy,
R211 is halogen or 1–4C-alkoxy,
R22 is halogen, 1–4C-alkyl or 1–4C-alkoxy,
R23 is halogen, 1–4C-alkyl or 1–4C-alkoxy,
R24 is halogen, 1–4C-alkyl or 1–4C-alkoxy,
R3 is halogen, 1–4C-alkyl or 1–4C-alkoxy,
R4 is halogen, amino, 1–4C-alkyl, 1–4C-alkoxy or phenyl,
R5 is halogen, 1–4C-alkyl or 1–4C-alkoxy,
or a hydrate, solvate, salt, hydrate of a salt, solvate of a salt, N-oxide or salt of an N-oxide thereof.

2. A compound of formula I according to claim 1 in which
R1 is 1–4C-alkoxy,
A is 1–4C-alkylene, B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where R2 is chlorine, bromine, fluorine, hydroxyl, nitro, amino, 1–7C-alkyl, trifluoromethyl, 3–7C-cycloalkyl, 3–7C-cycloalkyl-1–4C-alkyl, 1–4C-alkoxy, 1–4C-alkoxy which is completely or predominantly substituted by fluorine, 1–4C-alkoxy-1–4C-alkyl, 1–4C-alkoxy-1–4C-alkoxy, mono- or di-1–4C-alkylaminocarbonyl, mono- or di-1–4C-alkylaminosulfonyl, 1–4C-alkylcarbonylamino, 1–4C-alkylsulfonylamino, phenyl, phenyl substituted by R21, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where R21 is cyano, chlorine, bromine, fluorine, carboxyl, 1–4C-alkyl, 1–4C-alkoxy, aminocarbonyl, mono- or di-1–4C-alkylaminocarbonyl, 1–4C-alkylcarbonylamino, 1–4C-alkoxycarbonyl, aminosulfonyl or mono- or di-1–4C-alkylaminosulfonyl, R22 is chlorine, bromine, fluorine, 1–4C-alkyl or 1–4C-alkoxy, R23 is chlorine, bromine, fluorine, 1–4C-alkyl or 1–4C-alkoxy, R24 is chlorine, bromine, fluorine, 1–4C-alkyl or 1–4C-alkoxy, R3 is chlorine, bromine, fluorine, 1–4C-alkyl or 1–4C-alkoxy, R4 is chlorine, bromine, fluorine, 1–4C-alkyl, 1–4C-alkoxy or phenyl, R5 is chlorine, bromine, fluorine, 1–4C-alkyl or 1–4C-alkoxy, or a hydrate, solvate, salt, hydrate of a salt, solvate of a salt, N-oxide or salt of an N-oxide thereof.

3. A compound of formula I according to claim 1 in which
R1 is methoxy,
A is ethylene,
B represents 3H-imidazo[4,5-b]pyridin-2-yl, 3H-imidazo[4,5-b]pyridin-2-yl substituted by R2 and/or R3, 9H-purin-8-yl or 9H-purin-8-yl substituted by R4 and/or R5, where R2 is halogen, hydroxyl, nitro, 1–7C-alkyl, trifluoromethyl, 3–7C-cycloalkyl, 3–7C-cycloalkyl-1–4C-alkyl, 1–4C-alkoxy, 1–4C-alkoxy which is completely or predominantly substituted by fluorine, 1–4C-alkoxy-1–4C-alkyl, 1–4C-alkoxy-1–4C-alkoxy, 1–4C-alkoxycarbonyl, phenyl, phenyl substituted by R21 and/or R211, phenyl-1–4C-alkyl, phenyl-1–4C-alkyl wherein the phenyl moiety is substituted by R22, phenyl-1–4C-alkoxy, pyridyl, pyridyl substituted by R23, pyridyl-1–4C-alkyl, pyridyl-1–4C-alkyl wherein the pyridyl moiety is substituted by R24, where R21 is cyano, halogen, carboxyl, 1–4C-alkyl, 1–4C-alkoxy, aminocarbonyl, mono- or di-1–4C-alkylaminocarbonyl, 1–4C-alkylcarbonylamino, 1–4C-alkoxycarbonyl, amino, mono- or di-1–4C-alkylamino, trifluoromethyl, hydroxyl, phenylsulfonylamino or phenyl-1–4C-alkoxy, R211 is halogen or 1–4C-alkoxy,
R22 is halogen, 1–4C-alkyl or 1–4C-alkoxy,
R23 is 1–4C-alkyl,
R24 is halogen, 1–4C-alkyl or 1–4C-alkoxy,
R3 is halogen, 1–4C-alkyl or 1–4C-alkoxy,
R4 is halogen, 1–4C-alkyl or 1–4C-alkoxy,
R5 is halogen or 1–4C-alkyl, or a hydrate, solvate, salt, hydrate of a salt, solvate of a salt, N-oxide or salt of an N-oxide thereof.

4. A compound of formula I according to claim 1 in which
R1 is methoxy,
A is ethylene,
B represents 3H-imidazo[4,5-b]pyridin-2-yl, 3H-imidazo[4,5-b]pyridin-2-yl substituted by R2 and/or R3, or 9H-purin-8-yl, where R2 is halogen, hydroxyl, nitro, 1–7C-alkyl, trifluoromethyl, 3–7C-cycloalkyl-1–4C-alkyl, 1–4C-alkoxy, 1–4C-alkoxy which is completely or predominantly substituted by fluorine, 1–4C-alkoxy-1–4C-alkoxy, 1–4C-alkoxycarbonyl, phenyl, phenyl substituted by R21 and/or R211, phenyl-1–4C-alkyl, phenyl-1–4C-alkyl wherein the phenyl moiety is substituted by R22, phenyl-1–4C-alkoxy, pyridyl, pyridyl-1–4C-alkyl, pyridyl-1–4C-alkyl wherein the pyridyl moiety is substituted by R24, where R21 is cyano, halogen, carboxyl, 1–4C-alkyl, 1–4C-alkoxy, 1–4C-alkylcarbonylamino, 1–4C-alkoxycarbonyl, amino, mono- or di-1–4C-alkylamino, trifluoromethyl, hydroxyl, phenylsulfonylamino or phenyl-1–4C-alkoxy, R211 is halogen or 1–4C-alkoxy,
R22 is halogen or 1–4C-alkyl,
R24 is 1–4C-alkoxy,
R3 is 1–4C-alkyl, or a hydrate, solvate, salt, hydrate of a salt, solvate of a salt, N-oxide or salt of an N-oxide thereof.

5. A compound of formula I according to claim 1 in which
R1 is methoxy,
A is ethylene,
B represents 3H-imidazo[4,5-b]pyridin-2-yl, 7-methyl-3H-imidazo[4,5-b]pyridin-2-yl, 5,7-dimethyl-3H-imidazo[4,5-b]pyridin-2-yl, 5-methoxy-3H-imidazo[4,5-b]pyridin-2-yl, 6-bromo-3H-imidazo[4,5-b]pyridin-2-yl or 9H-purin-8-yl, or a hydrate, solvate, salt, hydrate of a salt, solvate of a salt, N-oxide or salt of an N-oxide thereof.

6. A compound according to claim 1 selected from the group consisting of

2-[2-(4-methoxypyridin-2-yl)ethyl]-3H-imidazo[4,5-b]pyridine,
8-[2-(4-methoxypyridin-2-yl)ethyl]-9H-purine,
2-[2-(4-methoxypyridin-2-yl)ethyl]-7-methyl-3H-imidazo[4,5-b]pyridine,
2-[2-(4-methoxypyridin-2-yl)ethyl]-5,7-dimethyl-3H-imidazo[4,5-b]pyridine,
2-[2-(4-methoxypyridin-2-yl)ethyl]-5-methoxy-3H-imidazo[4,5-b]pyridine,
2-[2-(4-methoxypyridin-2-yl)ethyl]-6-bromo-3H-imidazo[4,5-b]pyridine,
2-[2-(4-methoxypyridin-2-yl)ethyl]-6-iodo-3H-imidazo[4,5-b]pyridine,
2-[2-(4-methoxypyridin-2-yl)ethyl]-6-nitro-3H-imidazo[4,5-b]pyridine,
2-[2-(4-methoxypyridin-2-yl)ethyl]-6-trifluoromethyl-3H-imidazo[4,5-b]pyridine,
2-[2-(4-methoxypyridin-2-yl)ethyl]-6-phenyl-3H-imidazo[4,5-b]pyridine,
2-[2-(4-methoxypyridin-2-yl)ethyl]-6-methyl-3H-imidazo[4,5-b]pyridine,
2-[2-(4-methoxypyridin-2-yl)ethyl]-6-(2-methylpropyl)-3H-imidazo[4,5-b]pyridine,
2-[2-(4-methoxypyridin-2-yl)ethyl]-6-cyclohexylmethyl-3H-imidazo[4,5-b]pyridine, 2-[2-(4-methoxypyridin-2-yl)ethyl]-6-(2-phenylethyl)-3H-imidazo[4,5-b]pyridine,
2-[2-(4-methoxypyridin-2-yl)ethyl]-6-(3,4-dichlorphenyl)-3H-imidazo[4,5-b]pyridine,
2-[2-(4-methoxypyridin-2-yl)ethyl]-6-(4-bromphenyl)-3H-imidazo[4,5-b]pyridine,
2-[2-(4-methoxypyridin-2-yl)ethyl]-6-(4-brombenzyl)-3H-imidazo[4,5-b]pyridine,
7-(2-methoxyethoxy)-2-[2-(4-methoxypyridin-2-yl)ethyl]-3H-imidazo[4,5-b]pyridine,
2-[2-(4-methoxypyridin-2-yl)ethyl]-7-(2-phenylethoxy)-3H-imidazo[4,5-b]pyridine,
2-[2-(4-methoxypyridin-2-yl)ethyl]-7-(2,2,2-trifluoroethoxy)-3H-imidazo[4,5-b]pyridine,
7-hydroxy-2-[2-(4-methoxypyridin-2-yl)ethyl]-3H-imidazo[4,5-b]pyridine,
2-[2-(4-methoxypyridin-2-yl)ethyl]-7-(2-p-tolylethyl)-3H-imidazo[4,5-b]pyridine,
2,7-bis-[2-(4-methoxypyridin-2-yl)ethyl]-3H-imidazo[4,5-b]pyridine,
2-[2-(4-methoxypyridin-2-yl)ethyl]-7-(2-pyridin-yl-ethyl)-3H-imidazo[4,5-b]pyridine,
2-[2-(4-methoxypyridin-2-yl)ethyl]-6-p-tolyl-3H-imidazo[4,5-b]pyridine,
2-[2-(4-methoxypyridin-2-yl)ethyl]-6-(pyridin-3-yl)-3H-imidazo[4,5-b]pyridine,
2-[2-(4-methoxypyridin-2-yl)ethyl]-6-(4-aminophenyl)-3H-imidazo[4,5-b]pyridine,
2-[2-(4-methoxypyridin-2-yl)ethyl]-6-(4-hydroxyphenyl)-3H-imidazo[4,5-b]pyridine,
2-[2-(4-methoxypyridin-2-yl)ethyl]-6-(4-N,N-dimethylaminophenyl)-3H-imidazo[4,5-b]pyridine,
2-[2-(4-methoxypyridin-2-yl)ethyl]-6-(4-trifluormethylphenyl)-3H-imidazo[4,5-b]pyridine,
2-[2-(4-methoxypyridin-2-yl)ethyl]-6-(3,4-dimethoxyphenyl)-3H-imidazo[4,5-b]pyridine,
2-[2-(4-methoxypyridin-2-yl)ethyl]-6-(4-benzyloxyphenyl)-3H-imidazo[4,5-b]pyridine,
2-[2-(4-methoxypyridin-2-yl)ethyl]-6-(4-benzyloxy-3-fluorophenyl)-3H-imidazo[4,5-b]pyridine,
2-[2-(4-methoxypyridin-2-yl)ethyl]-6-(4-cyanophenyl)-3H-imidazo[4,5-b]pyridine,
2-[2-(4-methoxypyridin-2-yl)ethyl]-3H-imidazo[4,5-b]pyridine-6-carboxylic acid methyl ester,
N-(4-{2-[2-(4-methoxypyridin-2-yl)ethyl]-3H-imidazo[4,5-b]pyridine-6-yl}phenyl)-acetamide,
N-(4-{2-[2-(4-methoxypyridin-2-yl)ethyl]-3H-imidazo[4,5-b]pyridine-6-yl}phenyl)-benzenesulfonamide,
2-[2-(4-methoxy-1-oxy-pyridin-2-yl)ethyl]-3H-imidazo[4,5-b]pyridine, and the hydrates, solvates, salts, hydrates of the salts, and solvates of the salts thereof.

7. A pharmaceutical composition containing one or more compounds of formula I according to claim 1, or a pharmaceutically acceptable hydrate, solvate, salt, hydrate of a salt, solvate of a salt, N-oxide or salt of an N-oxide thereof, together with a pharmaceutically acceptable auxiliary and/or excipient.

8. A method for treating an acute inflammatory disease in which the activity of inducible NO-synthase is involved in a patient comprising administering to said patient a therapeutically effective amount of a compound of formula I according to claim 1 or a pharmaceutically acceptable hydrate, solvate, salt, hydrate of a salt, solvate of a salt, N-oxide or salt of an N-oxide thereof.

9. A method for treating a chronic inflammatory disease of a peripheral organ and/or the central nervous system (CNS) in which the activity of inducible NO-synthase is involved in a patient comprising administering to said patient a therapeutically effective amount of a compound of formula I according to claim 1 or a pharmaceutically acceptable hydrate, solvate, salt, hydrate of a salt, solvate of a salt, N-oxide or salt of an N-oxide thereof.

10. A method for treating a disease of disorder selected from the group consisting of sepsis, inflammatory skin conditions, inflammatory eye conditions, gastrointestinal inflammatory diseases, lung inflammatory diseases, arthritic disorders and heart disorders in a patient comprising administering to said patient a therapeutically effective amount of a compound of formula I according to claim 1 or a pharmaceutically acceptable hydrate, solvate, salt, hydrate of a salt, solvate of a salt, N-oxide or salt of an N-oxide thereof.

* * * * *

UNITED STATES PATENT AND TRADEMARK OFFICE
CERTIFICATE OF CORRECTION

PATENT NO. : 7,138,399 B2
APPLICATION NO. : 10/509396
DATED : November 21, 2006
INVENTOR(S) : Ulrich It is certified that error appears in the above-identified patent and that said Letters Patent is hereby corrected as shown below:

Claim 10, Column 40, Line 32,
Please delete " disease of disorder " and
replace with -- disease or disorder --

Signed and Sealed this

Twenty-fourth Day of April, 2007

JON W. DUDAS
*Director of the United States Patent and Trademark Office*